(12) United States Patent (10) Patent No.: US 8,140,149 B2
Hatakeyama et al. (45) Date of Patent: Mar. 20, 2012

(54) DROWSINESS DETECTOR

(75) Inventors: Yoshiyuki Hatakeyama, Fuji (JP);
Shintaro Yoshizawa, Gotemba (JP)

(73) Assignee: Toyota Jidosha Kabushiki Kaisha,
Aichi (JP)

( * ) Notice: Subject to any disclaimer, the term of this
patent is extended or adjusted under 35
U.S.C. 154(b) by 0 days.

(21) Appl. No.: 13/001,774

(22) PCT Filed: Jul. 2, 2009

(86) PCT No.: PCT/JP2009/062131
§ 371 (c)(1),
(2), (4) Date: Dec. 28, 2010

(87) PCT Pub. No.: WO2010/001962
PCT Pub. Date: Jan. 7, 2010

(65) Prior Publication Data
US 2011/0105925 A1 May 5, 2011

(30) Foreign Application Priority Data

Jul. 4, 2008 (JP) .................................. 2008-175953
Dec. 2, 2008 (JP) .................................. 2008-307455
Dec. 2, 2008 (JP) .................................. 2008-307460

(51) Int. Cl.
*A61B 5/0402* (2006.01)
(52) U.S. Cl. ..................................................... 600/509
(58) Field of Classification Search ............... 340/573.1,
340/575; 600/300, 485, 508, 509
See application file for complete search history.

(56) References Cited

U.S. PATENT DOCUMENTS
2005/0246134 A1 11/2005 Nagai et al.

FOREIGN PATENT DOCUMENTS

| JP | 1-126206 U | 8/1989 |
|---|---|---|
| JP | 03-272745 A | 12/1991 |
| JP | 05-228121 A | 9/1993 |
| JP | 06-278495 A | 10/1994 |
| JP | 2003-245357 A | 9/2003 |
| JP | 2005-080970 A | 3/2005 |
| JP | 2005-095408 A | 4/2005 |

(Continued)

OTHER PUBLICATIONS

Notification of Transmittal of Translation of the International Preliminary Report on Patentability (IPRP) issued on Mar. 24, 2011 in corresponding PCT/JP2009/062131.

(Continued)

*Primary Examiner* — Carl H Layno
*Assistant Examiner* — Allen Porter, Jr.
(74) *Attorney, Agent, or Firm* — Sughrue Mion, PLLC

(57) ABSTRACT

A drowsiness detector capable of detecting light drowsiness of a subject with high precision is provided. The drowsiness detector acquires the measurement data of a measurement device first, and acquires a value of the pulse rate by performing preprocessing on the measurement data and extracts a pulse fluctuation from the value of the pulse rate. Then, the drowsiness detector sets the reference section width of the pulse feature value referred to in order to acquire the standard deviation of the pulse feature value (value of the pulse rate and pulse fluctuation) and then calculates the standard deviation value of the pulse feature value in the reference section width and acquires the corrected standard deviation value of the pulse feature value by dividing the standard deviation value of the pulse feature value by the pulse feature value. Then, the drowsiness detector determines whether or not the driver is lightly drowsy using the corrected standard deviation value of the pulse feature value.

14 Claims, 43 Drawing Sheets

FOREIGN PATENT DOCUMENTS

| | | |
|---|---|---|
| JP | 2005-312653 A | 11/2005 |
| JP | 2006-223635 A | 8/2006 |
| JP | 2007-006970 A | 1/2007 |
| JP | 2007-044154 A | 2/2007 |
| JP | 2007-105111 A | 4/2007 |
| JP | 2008-035964 A | 2/2008 |
| JP | 2008-161664 A | 7/2008 |
| JP | 2008-188108 A | 8/2008 |
| WO | 2008/069337 A1 | 6/2008 |
| WO | 2008/114865 A1 | 9/2008 |

OTHER PUBLICATIONS

Yoshiyuki Hatakeyama, et al., "Development of Judgment Technology for Shallow Drowsiness", Oct. 22, 2008, pp. 1-4, English Abstract.

Fig.3

| AUTONOMIC NERVE | RELATED PULSE FEATURE VALUE | | |
|---|---|---|---|
| SYMPATHETIC NERVE | PULSE FLUCTUATION LOW-FREQUENCY COMPONENT (HRV-L) | L/H $\left[ = \dfrac{\text{HRV-L}}{\text{HRV-H}} \right]$ | |
| PARASYMPATHETIC NERVE | PULSE FLUCTUATION HIGH-FREQUENCY COMPONENT (HRV-H) | PULSE RATE | |

| TIME | 1 | 2 | 3 | 4 |
|---|---|---|---|---|
| PULSE RATE STANDARD DEVIATION VALUE | 10.40 | 9.80 | 11.50 | 16.00 |
| VALUE OF PULSE RATE | 74.50 | 74.50 | 74.50 | 74.50 |

(B)

| TIME | 1 | 2 | 3 | 4 |
|---|---|---|---|---|
| CORRECTED PULSE RATE STANDARD DEVIATION VALUE | 0.14 | 0.13 | 0.15 | 0.21 |

| TIME | 1 | 2 | 3 | 4 |
|---|---|---|---|---|
| PULSE RATE STANDARD DEVIATION VALUE | 10.40 | 9.80 | 11.50 | 16.00 |
| VALUE OF PULSE RATE | 74.50 | 79.00 | 70.30 | 81.80 |

(B)

| TIME | 1 | 2 | 3 | 4 |
|---|---|---|---|---|
| CORRECTED PULSE RATE STANDARD DEVIATION VALUE | 0.14 | 0.12 | 0.16 | 0.20 |

(A)

(B)

(A)

(B)

US 8,140,149 B2

DROWSINESS DETECTOR

TECHNICAL FIELD

The present invention relates to a drowsiness detector which detects drowsiness of a driver of a vehicle, for example.

BACKGROUND ART

As a conventional drowsiness detector, for example, one disclosed in Patent Document 1 is known. A drowsiness detector described in Patent Document 1 determines whether or not a driver is in a nap state by measuring an index (pulse or the like) indicating the conditions for determining drowsiness of a driver, extracting from the index the feature value which changes with drowsiness of the driver, and comparing the feature value with a threshold value. When extracting the feature value from the pulse, an amplitude power spectrum is generated by performing Fourier transform on the time-series data of a pulse period, the time-series data of a pulse fluctuation is acquired by performing integration processing on the amplitude power spectrum, differential processing is performed on the time-series data of the pulse fluctuation, a threshold value is calculated from the average value and the standard deviation of differential values of the pulse fluctuation, and the excess of the differential value of the pulse fluctuation over the threshold value is extracted as the feature value.

Citation List

Patent Literature

Patent Document 1: Japanese Unexamined Patent Application Publication No. 2008-35964

SUMMARY OF INVENTION

Technical Problem

In the conventional technique described above, however, when a driver (subject) is resisting very light drowsiness, for example, while driving, it may not be possible to correctly determine that the driver is in a drowsy state.

Therefore, the present invention provides a drowsiness detector capable of detecting light drowsiness of a subject with high precision.

Solution to Problem

The inventor and others found out that as a result of repeated careful examination regarding drowsiness of a driver, it was effective to pay attention to the pulse feature value influenced by the activity of the autonomic nerve relevant to the occurrence of drowsiness, such as a pulse rate and a pulse fluctuation, in order to determine light drowsiness. Moreover, further examination showed that the statistical amount indicating the size of a fluctuation in the pulse feature value, such as a standard deviation, was a feature value capable of expressing a state where two physical functions, activation of the body by a sympathetic nervous system and stabilization of the body by a parasympathetic nervous system conflicted with each other dynamically, and correlated with light drowsiness. The present invention is made on the basis of such findings.

That is, a drowsiness detector of the present invention is characterized in that a measurement means for measuring a heartbeat or a pulse of a subject, a pulse feature value extracting means for extracting the pulse feature value from the heartbeat or the pulse measured by the measurement means, a variation distribution calculating means for calculating variation distribution of the pulse feature value extracted by the pulse feature value extracting means, and a drowsiness level determining means for determining a drowsiness level of the subject using the variation distribution of the pulse feature value calculated by the variation distribution calculating means are provided.

In such a drowsiness detector of the present invention, the heartbeat or a pulse of a subject is measured, the pulse feature value is extracted from the measurement data, the variation distribution of the pulse feature value is calculated, and the drowsiness level of the subject is determined using the variation distribution of the pulse feature value. By determining the drowsiness using the variation distribution of the pulse feature value correlated with light drowsiness as described above, light drowsiness of the subject can be detected with high precision.

Preferably, the variation distribution calculating means calculates a standard deviation of the pulse feature value as the variation distribution of the pulse feature value, and the drowsiness level determining means determines the drowsiness level of the subject on the basis of the standard deviation of the pulse feature value. In this case, the drowsiness level of the subject can be determined easily and reliably by comparing the standard deviation of the pulse feature value with the threshold value for drowsiness determination set in advance, for example.

In addition, an average value calculating means for calculating an average value of the pulse feature value extracted by the pulse feature value extracting means may be further provided. The variation distribution calculating means may calculate a standard deviation of the pulse feature value as the variation distribution of the pulse feature value, and the drowsiness level determining means may determine the drowsiness level of the subject on the basis of the standard deviation of the pulse feature value and the average value of the pulse feature value. In this case, the drowsiness level of the subject can be determined easily and reliably by generating a distribution, which expresses drowsiness, from a matrix (two-dimensional coordinates) of the average value and the standard deviation of the pulse feature value, for example.

Here, preferably, a reference time width setting means for setting a reference time width of the pulse feature value referred to in order to obtain the standard deviation of the pulse feature value may be further provided. The variation distribution calculating means may calculate the standard deviation of the pulse feature value within the reference time width of the pulse feature value. In this case, detection of drowsiness which does not depend on a subject can be realized by setting the reference time width of the pulse feature value to the optimal value for every subject and calculating the standard deviation of the pulse feature value within the reference time width.

At this time, it is preferable that the reference time width setting means extracts a peak frequency by frequency analysis of the pulse feature value and sets a period corresponding to the peak frequency as the reference time width. In this case, the optimal reference time width can be reliably set for every subject by extracting the peak frequency within the frequency range of the pulse feature value expected when drowsiness appears noticeably for every subject.

Moreover, preferably, the variation distribution calculating means has a means for correcting the standard deviation of the pulse feature value by dividing the standard deviation of the pulse feature value by the pulse feature value. Since the pulse feature value, such as a pulse rate, differs with each subject, the standard deviation of the pulse feature value also differs with each subject. For this reason, a result of drowsiness detection may differ depending on a subject. Therefore, by performing a correction of dividing the standard deviation of the pulse feature value by the pulse feature value so that a determination error of the drowsiness level caused by the difference of the pulse feature value of each subject is eliminated, detection of drowsiness which does not depend on a subject can be performed with sufficient precision.

In addition, preferably, the pulse feature value includes at least one of a pulse rate, a pulse fluctuation low-frequency component relevant to the activity of a sympathetic nerve, a pulse fluctuation high-frequency component relevant to the activity of a parasympathetic nerve, and a ratio of the pulse fluctuation low-frequency component and the pulse fluctuation high-frequency component. A characteristic of the pulse feature value differs with each subject, such as a person with a pulse in which the drowsiness level appears noticeably, a person with an active sympathetic nerve, and a person with an active parasympathetic nerve. Accordingly, light drowsiness of the subject can be detected with higher precision by determining the drowsiness level using the pulse feature value suitable for the subject.

Moreover, in a drowsiness detector which detects drowsiness of a driver of a vehicle, it is preferable that a standard deviation calculating means for calculating a standard deviation of the pulse feature value extracted by the pulse feature value extracting means is provided and the drowsiness level determining means corrects the standard deviation of the pulse feature value with the pulse feature value according to a traveling environment of the vehicle and determines the drowsiness level of the driver using the distribution of a standard deviation of the pulse feature value after correction.

In order to detect light drowsiness, it is effective to pay attention to the pulse feature value influenced by the autonomic nerve activity relevant to the occurrence of drowsiness, such as a pulse rate and a pulse fluctuation. Particularly, it is thought that the standard deviation of the pulse feature value correlates with light drowsiness. Therefore, in the drowsiness detector of the present invention, the standard deviation of the pulse feature value extracted by the pulse feature value extracting means is calculated, and the drowsiness level of the driver is determined using the distribution of the standard deviation of the pulse feature value.

Here, since the pulse feature value differs with each driver, the standard deviation of the pulse feature value also differs with each driver. For this reason, a result of drowsiness detection may differ with each driver. Accordingly, a determination error of the drowsiness level caused by the difference of the pulse feature value of each driver is eliminated by correcting the standard deviation of the pulse feature value with the pulse feature value. At this time, a change in the pulse feature value caused by drowsiness occurs continuously for a relatively long period of time. Moreover, the pulse feature value changes even when the traveling environment of a vehicle changes, and the change in the pulse feature value caused by the traveling environment change occurs instantaneously. For this reason, the change in the pulse feature value caused by the traveling environment change may be a cause of noise when correcting the standard deviation of the pulse feature value (erroneous detection of drowsiness).

Therefore, in the present invention, the standard deviation of the pulse feature value is corrected with the pulse feature value according to the traveling environment of a vehicle. Specifically, an instantaneous change in the pulse feature value caused by a traveling environment change of a vehicle is removed as noise, and the standard deviation of the pulse feature value is corrected with the pulse feature value only when the pulse feature value changes due to the change of the driver's body state. As a result, light drowsiness of a driver can be detected with high precision.

Preferably, the drowsiness level determining means does not correct the standard deviation of the pulse feature value when it is detected that the vehicle travels in any of an urban area, a curved road, a road along which the driver has not driven previously, or through an intersection. When the vehicle travels in an urban area, a curved road, a road along which the driver has not driven previously, or an intersection, an instantaneous change in the pulse feature value easily occurs. Therefore, in such a case, light drowsiness of the driver can be reliably detected with high precision by not executing the correction of the standard deviation of the pulse feature value.

In addition, the drowsiness level determining means may not correct the standard deviation of the pulse feature value when it is detected that a moving object is present in the vicinity of the vehicle. When moving objects, such as other vehicles or pedestrians, are present in the vicinity of the vehicle, an instantaneous change in the pulse feature value tends to occur. Therefore, in such a case, light drowsiness of the driver can be reliably detected with high precision by not executing the correction of the standard deviation of the pulse feature value.

In addition, the drowsiness level determining means may not correct the standard deviation of the pulse feature value when it is detected that a passenger is in the vehicle and the driver is moving. When a passenger is in the vehicle and the driver is moving, an instantaneous change in the pulse feature value tends to occur. Therefore, in such a case, light drowsiness of the driver can be reliably detected with high precision by not executing the correction of the standard deviation of the pulse feature value.

Moreover, a drowsiness detector of the present invention is characterized in that a standard deviation of the pulse feature value is corrected with the pulse feature value obtained by excluding the pulse feature value acquired in the traveling environment where conscious attention tends to be stimulated.

In addition, it is preferable that a reference time width setting means for setting a feature value reference time width for referring to the pulse feature value is provided, the drowsiness level determining means calculates statistical distribution of the pulse feature value within the feature value reference time width and determines the drowsiness level of the subject, and the reference time width setting means generates frequency spectrum distribution of the pulse feature value by frequency analysis of the pulse feature value and calculates the feature value reference time width by extracting a frequency of a rising peak of the frequency spectrum.

In such a drowsiness detector of the present invention, when setting the feature value reference time width for referring to the extracted pulse feature value, the frequency spectrum distribution of the pulse feature value is generated by frequency analysis of the pulse feature value and a frequency of a rising peak of the frequency spectrum is extracted. The frequency of the rising peak of the frequency spectrum is a frequency at which features of the subject tend to appear. For this reason, by calculating the feature value reference time width from the frequency of the rising peak, it is possible to acquire the feature value reference time width suitable for a subject. Therefore, drowsiness detection which is not affected by individual difference can be performed by calculating the statistical distribution of the pulse feature value within the suitable feature value reference time width of each subject and determining the drowsiness level of the subject using the statistical distribution of the pulse feature value.

Preferably, the reference time width setting means extracts a peak frequency at which a spectrum becomes the maximum within a frequency range having an initial minimum value as a starting point in the frequency spectrum distribution. The peak frequency at which a spectrum becomes a maximum is a frequency at which features of the subject are the most apparent. For this reason, by calculating the feature value reference time width from the frequency of the rising peak, it is possible to acquire the feature value reference time width which is most suitable for a subject.

In addition, preferably, the reference time width setting means sets the inverse of the peak frequency as the feature value reference time width. In this case, the feature value reference time width suitable for a subject can be reliably acquired.

In addition, preferably, the drowsiness level determining means calculates a standard deviation of the pulse feature value as the statistical distribution of the pulse feature value. It is thought that the standard deviation, such as a pulse rate and a pulse fluctuation, correlates with light drowsiness. Therefore, light drowsiness of a subject can be detected with high precision by calculating the standard deviation of the pulse feature value within the feature value reference time width and determining the drowsiness level of the subject using the standard deviation of the pulse feature value.

Moreover, a drowsiness detector of the present invention extracts a peak indicating a feature of an individual from the frequency spectrum distribution of the pulse feature value and refers to the pulse feature value from a time width based on the peak frequency.

Advantageous Effects of Invention

According to the present invention, it becomes possible to detect light drowsiness of a subject with high precision.

BRIEF DESCRIPTION OF DRAWINGS

FIG. 3 is a table showing the correspondence between the pulse feature value and the autonomic nerve activity.

FIG. 16 is a table showing an example of a pulse rate standard deviation value, a value of the pulse rate, and a corrected pulse rate standard deviation value.

FIG. 30 is a table showing an example of a pulse rate standard deviation value, a value of the pulse rate, and a corrected pulse rate standard deviation value.

DESCRIPTION OF EMBODIMENTS

Hereinafter, preferred embodiments of a drowsiness detector related to the present invention will be described in detail with reference to the accompanying drawings.

Figure 1:
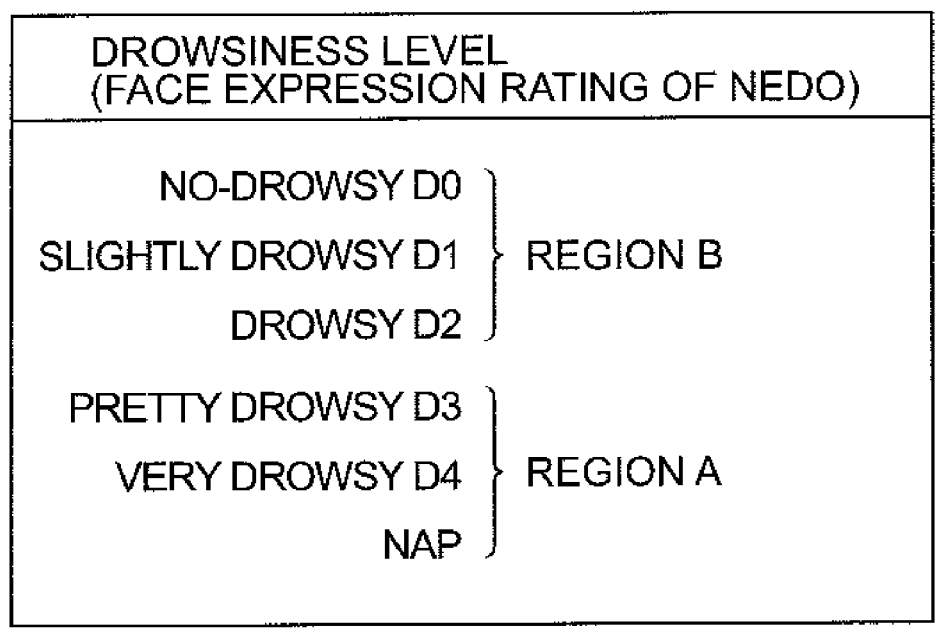
FIG. 1 is a table showing an example of human drowsiness levels.

First, the concept of drowsiness detection related to the present invention will be described. Human drowsiness levels may be divided into a region (region A) representing strongly drowsy states including a nap state, a very drowsy state (D4), and a moderately drowsy state (D3) and a region (region B) representing lightly drowsy states including a drowsy state (D2), a slightly drowsy state (D1), and a non-drowsy state (D0), for example, as shown in FIG. 1. In addition, the drowsiness levels shown in FIG. 1 are ratings from the facial expression of NEDO (refer to Research Center of Human Life Engineering: "Human Sense Measurement Manual", first volume, second article, p. 146 (1999)).

Although in recent years there have been developed some conventional techniques of determining a strongly drowsy state (region A) from the driver's facial direction or the blinking of driver's eyes, there is no conventional technique of determining the region (region B) representing a lightly drowsy state. Therefore, the applicability of the known blinking feature value for determination of the lightly drowsy state is examined here for the first time.

Figure 2:
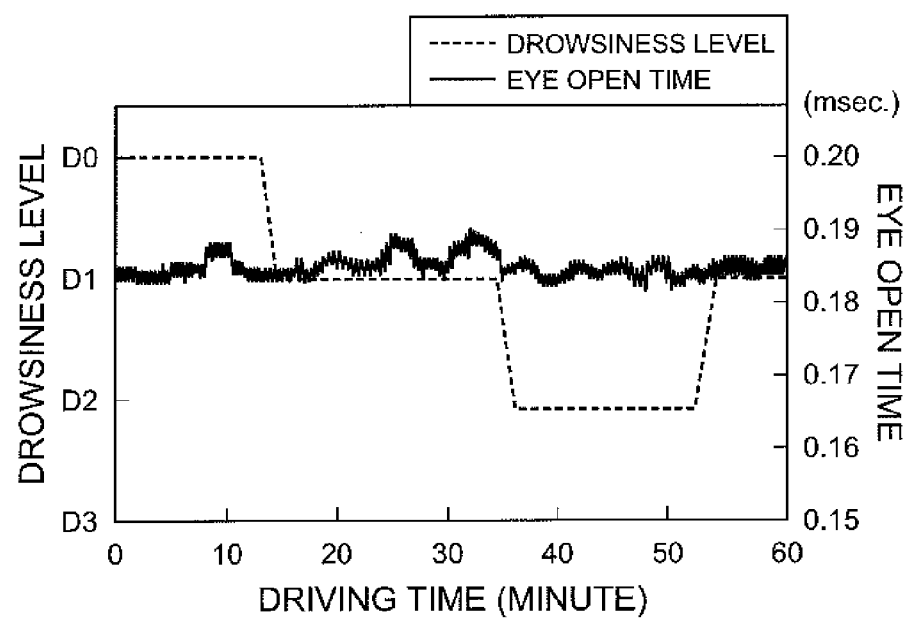
FIG. 2 is a graph showing an example of blinking data and drowsiness level data collected in a vehicle running test.

The known examination shows that the effective blinking feature value in the strongly drowsy state (region A) is an eye closing time (time taken for blinking once) and the number of blinks within a fixed time. Accordingly, the correspondence between both the blinking feature value and a drowsiness level change in a lightly drowsy state (region B) was examined. Specifically, regular traveling was performed in a predetermined circulating path course at a speed of 80 km/h for 1 hour and the drowsiness level data determined from the blinking data and the facial expression at that time was collected. An example of the collected data is shown in FIG. 2. Regarding the correlation coefficient between the drowsiness level and the blinking feature value, the eye closing time was 0.2 and the number of blinks was 0.1. Accordingly, it could be seen that it was difficult to determine light drowsiness only with the blinking feature value.

Therefore, it was thought that the influence of drowsiness would appear as a change of state inside the body, before appearing on the body, and attention was paid to the feature values inside the body.

As human characteristics inside the body which change with drowsiness, there are a brain information processing nerve activity which makes cognitive determinations and an autonomic nerve activity which manages a person's active state. The information processing nerve activity drops with drowsiness, but the occurrence of this drop in brain activity is accompanied by a change in the autonomic nerve activity. Accordingly, attention was paid to the activity of the autonomic nerve.

The autonomic nerve is formed by two nervous systems called a sympathetic nervous system which activates the body and a parasympathetic nervous system which stabilizes the body. In a nap state, the parasympathetic nervous system works actively in order to guide the body to rest. In the state where there is no drowsiness, the sympathetic nervous system works actively. Therefore, it was hypothesized that the balance of these two nervous systems changed according to the drowsiness levels D1 to D4 shown in FIG. 1.

Since the autonomic nerve runs through the core of the body, it is impossible to directly measure the activity itself. Accordingly, attention was paid to a pulse whose relationship with the autonomic nerve was clear medically and which could be measured. The pulse is influenced by the sympathetic nervous system and the parasympathetic nervous system and as a result, the pulsation (pulse rate, pulse fluctuation) of the pulse changes.

FIG. 3 shows a correspondence between the pulse feature value and the activity of the autonomic nerve. As the pulse feature value, there are a pulse fluctuation low-frequency component (HRV-L) relevant to the activity of the sympathetic nerve, a pulse fluctuation high-frequency component (HRV-H) relevant to the activity of the parasympathetic nerve, a ratio (hereinafter, L/H) between HRV-L and HRV-H indicating the balance thereof, and a pulse rate. These four pulse feature values are considered to be the feature values inside the body related with drowsiness.

Figure 4:
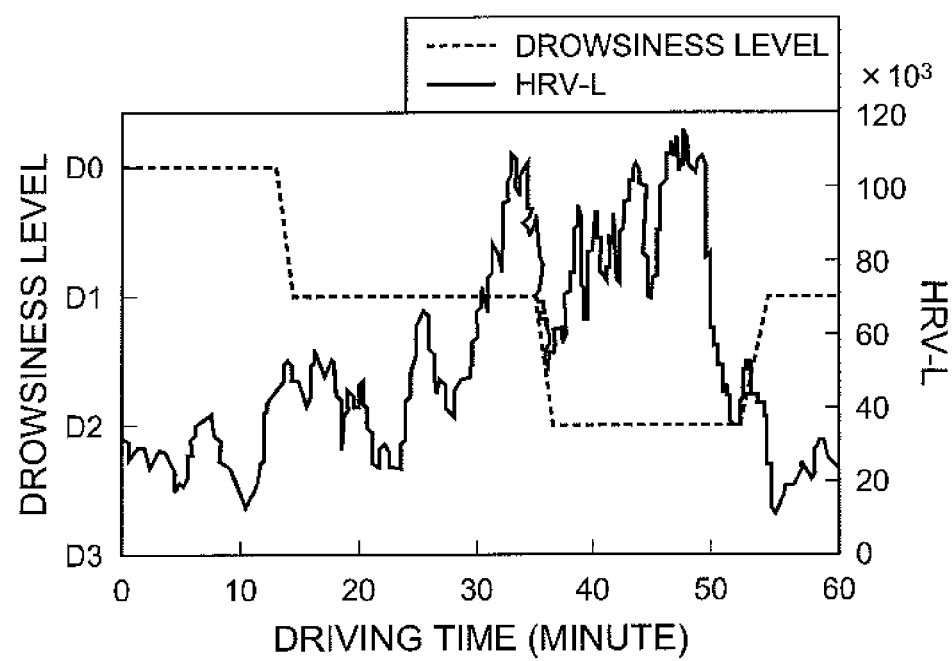
FIG. 4 is a graph showing an example of pulse data and drowsiness level data collected in a vehicle running test.

Regular traveling was performed in a predetermined circulating path course at a speed of 80 km/h for 1 hour, the drowsiness level data determined from the pulse data and the facial expression at that time was collected, and the correlation between the four pulse feature values and light drowsiness was verified using these data items. An example of the collected data is shown in FIG. 4.

As a result of having verified a correlation coefficient (Statistics of Bioscience: refer to Nankodo (2005)) as verification of the correlation, it could be seen that all of the four pulse feature values were correlated with light drowsiness even though this was a weak tendency. At this time, the correlation coefficients with respect to the drowsiness level were HRV-L: 0.5, HRV-H: 0.3, L/H: 0.3, pulse rate: 0.4, and a significant difference $p<0.05$. Accordingly, it could be seen that the drowsiness level correlated more with the pulse feature value inside the body than with the feature value outside the body, such as blinking, in the light drowsiness (region B).

It was thought that variations in the HRV-L, the HRV-H, the L/H, and the pulse rate, of which correlations with light drowsiness were expressed, were large because the correlation coefficients were not as high as described above. Accordingly, it was determined that it was difficult to determine light drowsiness in simple determination and analysis. Therefore, as a determination method which took the variation in data into consideration, a Mahalanobis-Taguchi method (hereinafter, an MT method) was used. An expression for evaluating the precision in drowsiness determination, which is adopted at this time, is as follows. Moreover, the following expression uses the drowsiness level D2 as an example.

Rate of determination of drowsiness level $D2$=(rate of correct answer)/(rate of correct answer+rate of incorrect answer)×100(%)

Rate of correct answer=(number of times answered correctly as D2 at the time of drowsiness level D2)/(number of all data items of drowsiness level D2)×100(%)

Rate of incorrect answer={(number of times answered incorrectly as D0,D1,D3,D4 at the time of drowsiness level D2)/(number of all data items of drowsiness level D2)+(number of times answered incorrectly as D2 at the time of drowsiness levels D0,D1,D3,D4)/(number of all data items of drowsiness levels D0,D1,D3,D4)}×100(%)  [Expression 1]

Figure 5:
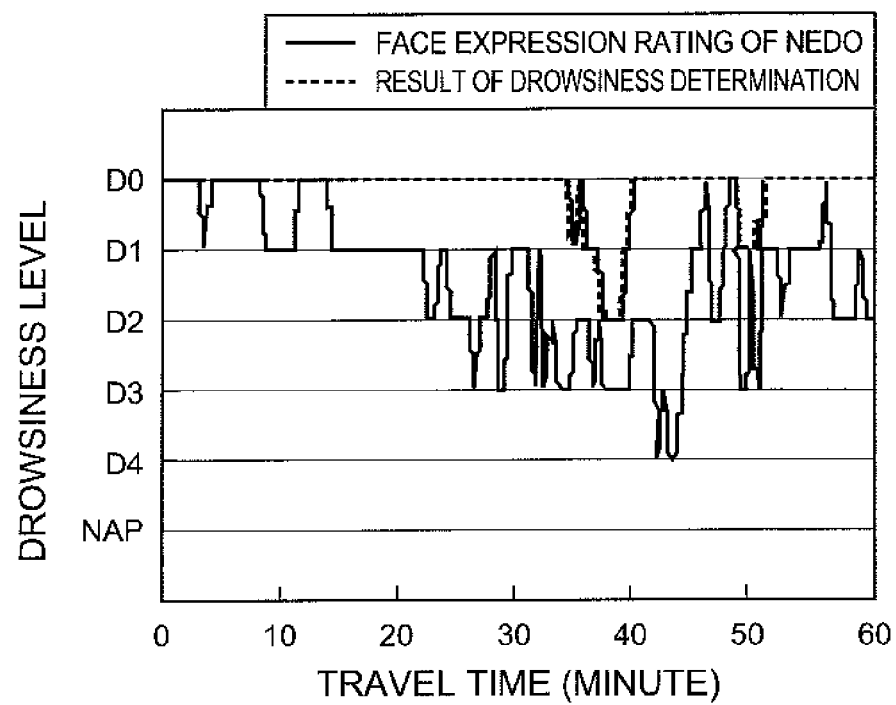
FIG. 5 is a graph showing an example of a result when light drowsiness was determined using the four feature values.

As a result of evaluation using the data obtained by a traveling test in which regular traveling was performed in a predetermined circulating path course at a speed of 80 km/h for 1 hour, the determination precision was 10%. An example of the determination result is shown in FIG. 5. Since there are lots of incorrect determinations in such a determination result, expansion of the feature value was considered in order to improve the determination precision.

The four pulse feature values described above are the feature values expressing a static state since the average value in a certain interval width is used. Accordingly, it is thought that the four pulse feature values cannot express a state where two physical functions, stimulation of the body for driving, such as a state of feeling drowsy during driving, and recuperation, which instinctively desires rest, conflict with each other dynamically. Therefore, a standard deviation indicating the size of a fluctuation in each of the four pulse feature values was thought to be the feature value indicating such a dynamic state.

As a result of having checked the correlation between the feature value indicating a dynamic state and the drowsiness level using the same method as for the feature value indicating the static state, it could be seen that each of the four feature values indicating a dynamic state was correlated with light drowsiness. At this time, the correlation coefficients with respect to the drowsiness level were a standard deviation of HRV-L: 0.4, a standard deviation of HRV-H: 0.4, a standard deviation of L/H: 0.3, a standard deviation of pulse rate: 0.4, and a significant difference p<0.05.

The MT method described above has guidelines concerning the evaluation of the S/N ratio (index of the degree of influences of noise, such as a variation, on a determination result) of a determination result to the combination of the extracted feature values and the selection of a proper combination of the feature values. Accordingly, based on the guidelines, the four feature values indicating a static state, the four feature values indicating a dynamic state, and the S/N ratio of these eight feature values were evaluated. As a result, the four feature values indicating a static state were −96 dB, the four feature values indicating a dynamic state were −95 dB, and the eight feature values were −89 dB. It could be seen that an improvement in the determination precision could be made using the eight feature values.

Figure 6:
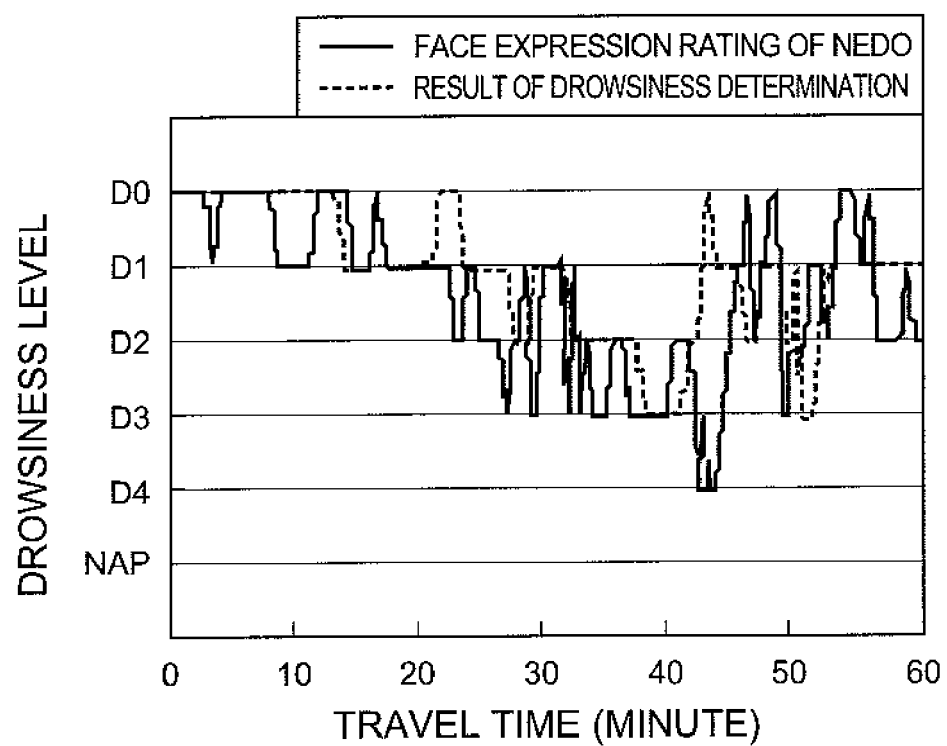
FIG. 6 is a graph showing an example of a result when light drowsiness was determined using the eight feature values.

Accordingly, light drowsiness determination was evaluated by the MT method using the eight feature values. As a result, the determination precision of 70% was acquired as shown in FIG. 6. That is, compared with the four feature values indicating a static state described above, an improvement in precision of 60% was made.

Based on the points of view described above, embodiments of a drowsiness detector related to the present invention will be described below.

[First Embodiment]

Figure 7:
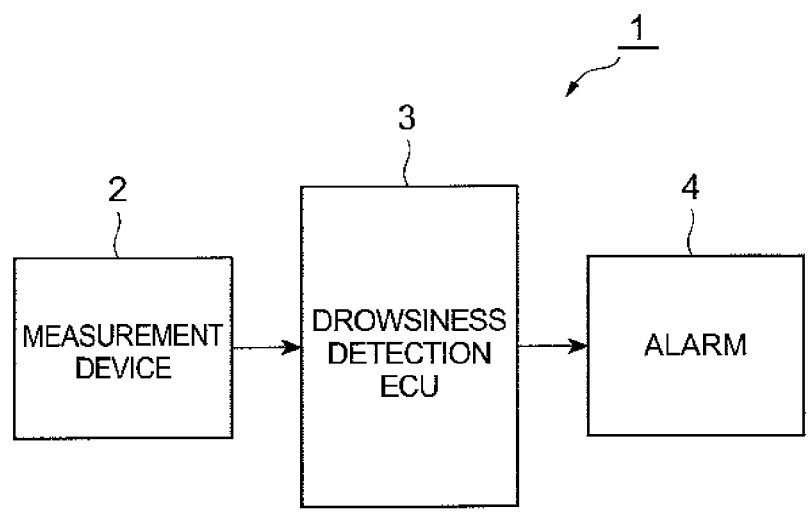
FIG. 7 is a block diagram showing the schematic configuration of a first embodiment of a drowsiness detector related to the present invention.

FIG. 7 is a block diagram showing the schematic configuration of a first embodiment of a drowsiness detector related to the present invention. In this drawing, a drowsiness detector 1 of the present embodiment is a device which is mounted in a vehicle and detects drowsiness of a driver of the vehicle. The drowsiness detector 1 includes a measurement device 2, a drowsiness detection ECU (Electronic Control Unit) 3, and an alarm 4.

The measurement device 2 is a device which measures a physiological index of the driver. Specifically, for example, an electrocardiogram system which measures a heartbeat and a plethysmograph which measures a pulse from the fingertip or forearm may be mentioned as the measurement device 2.

The drowsiness detection ECU 3 is configured to include a CPU, memories such as a ROM or a RAM, and an input and output circuit. The drowsiness detection ECU 3 is input with the measurement data of the measurement device 2, performs predetermined processing, and determines whether or not a driver is in a lightly drowsy state.

The alarm 4 is a device which notifies a driver of the occurrence of drowsiness by giving an alarm with a sound (buzzing sound), an image (screen display), vibration (vibrator), or the like.

Figure 8:
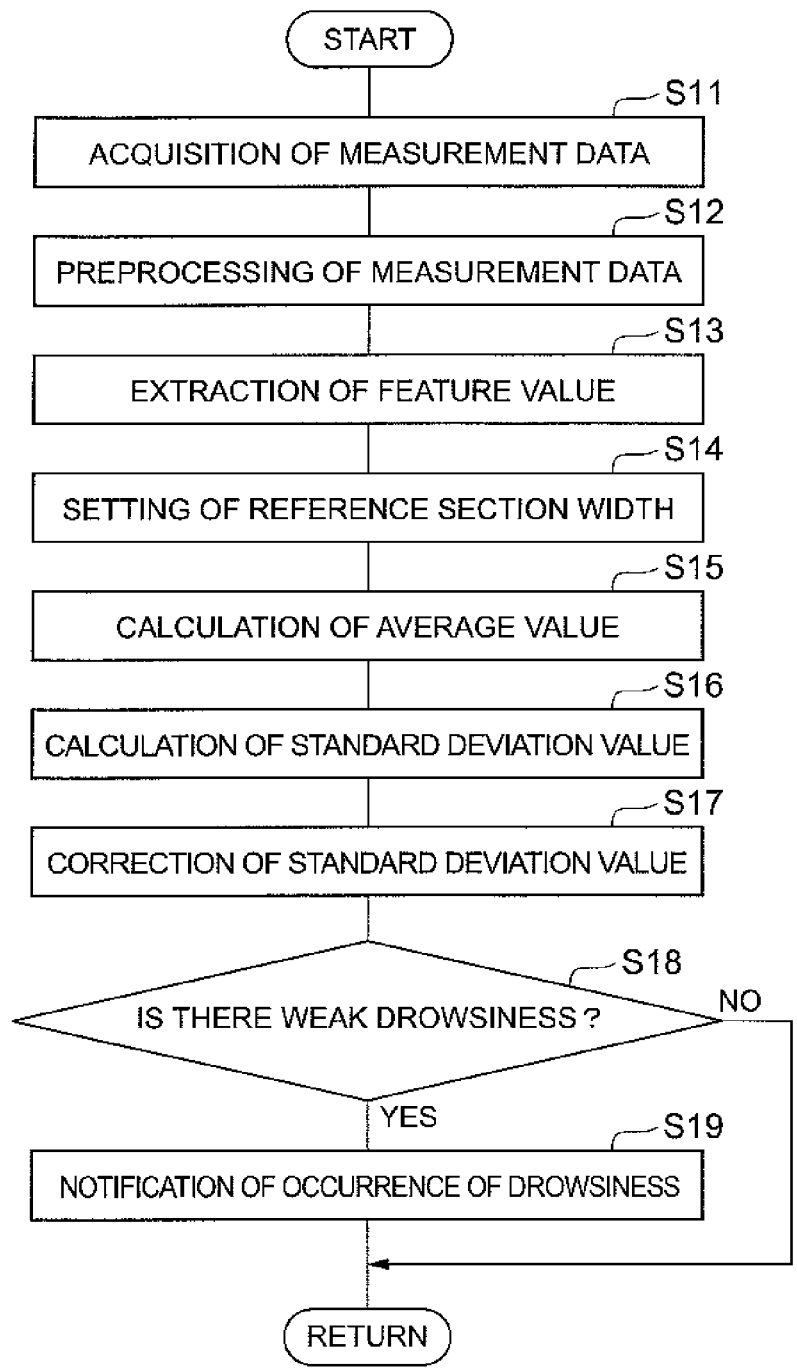
FIG. 8 is a flow chart showing the details of the procedure of drowsiness detection processing executed by a drowsiness detection ECU.

FIG. 8 is a flow chart showing the details of the procedure of drowsiness detection processing executed by the drowsiness detection ECU 3. Here, the case of measuring a pulse of a driver with an electrocardiogram system as the measurement device 2 will be described as an example.

In this drawing, the measurement data (raw pulse data) of the measurement device 2 is acquired first (step S11), and the measurement data is preprocessed (step S12). Specifically, first, components in a predetermined pass band (for example, 0.1 Hz to 30 Hz) are extracted by performing band pass filter (BPF) processing on the raw pulse data in order to remove noise of the pulse data.

Figure 9:
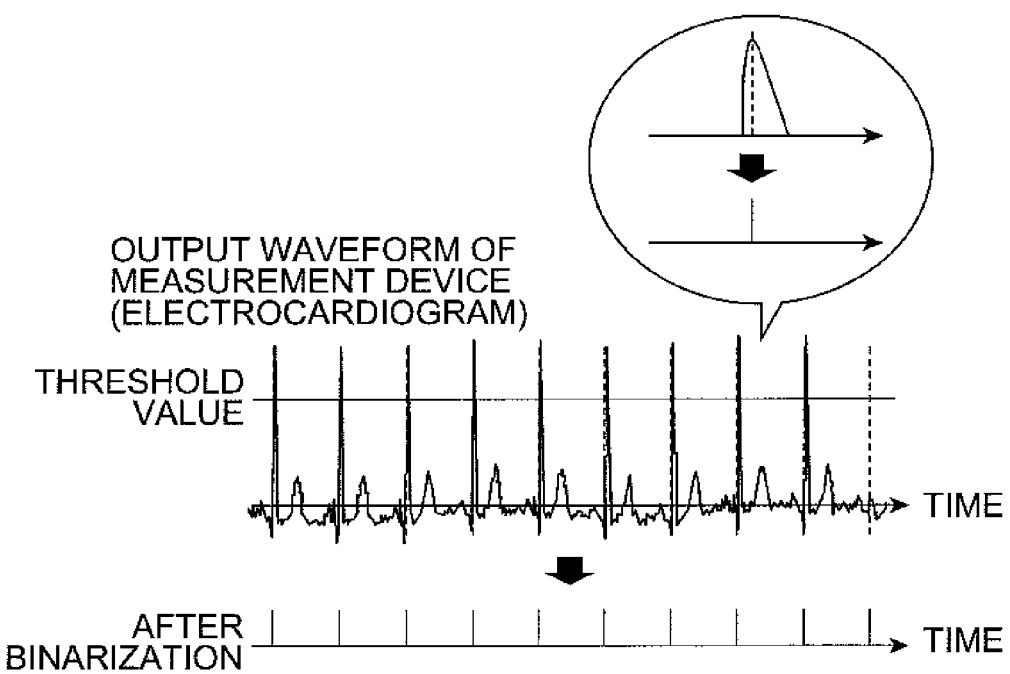
FIG. 9 is a waveform chart showing an example of an output waveform of a measurement device and a binarized waveform.

Then, as shown in FIG. 9, the waveform of the pulse data obtained by performing BPF processing is binarized by comparing it with the threshold value set in advance. At this time, the binarization is performed so that it becomes "1" at a timing when each R-wave portion of the waveform of the pulse data is a maximum (refer to the enlarged view in FIG. 9).

Figure 10:
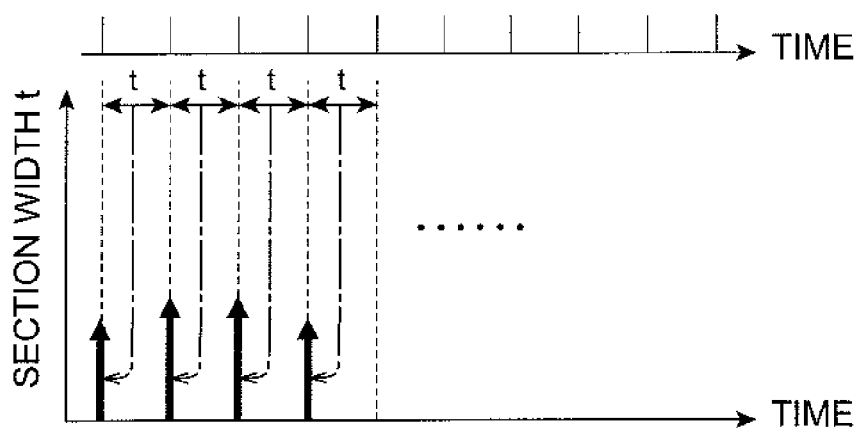
FIG. 10 is a waveform chart showing an example of the section width and a periodic time series of a binarized waveform.
Figure 10:
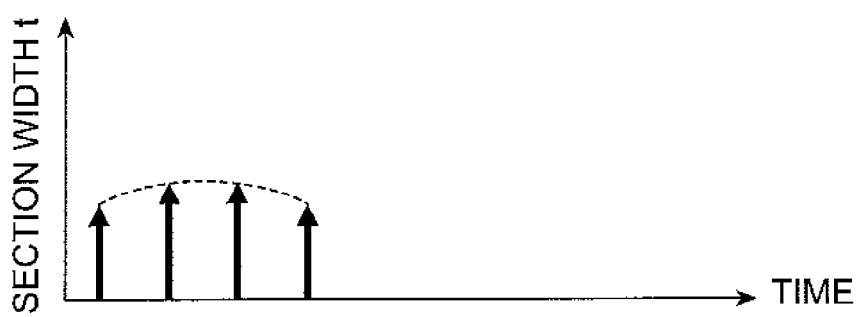

Then, as shown in FIG. 10A, a section width (time interval) t is calculated at each timing when the binary data becomes "1", and a graph having each section width t as a vertical axis is generated. At this time, the section width t is equivalent to a pulse period of a driver.

Figure 11:
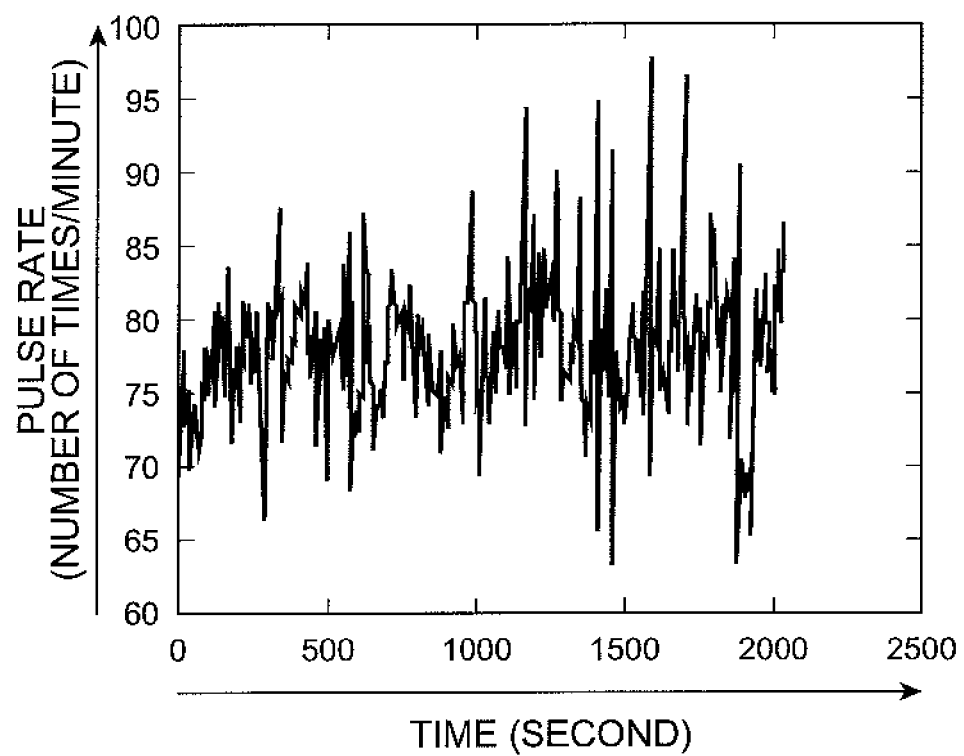
FIG. 11 is a waveform chart showing an example of a periodic time series of a pulse rate.

Then, as shown in FIG. 10B, a curve (refer to the broken line) of the pulse period is obtained by interpolating the graph of the pulse period, and the time-series data of the pulse period is acquired. Then, as shown in FIG. 11, the vertical axis unit of the time-series data of the pulse period is converted into the pulse rate per minute, for example. Accordingly, the value of the pulse rate of the driver can be acquired as one of the pulse feature values.

Figure 12:
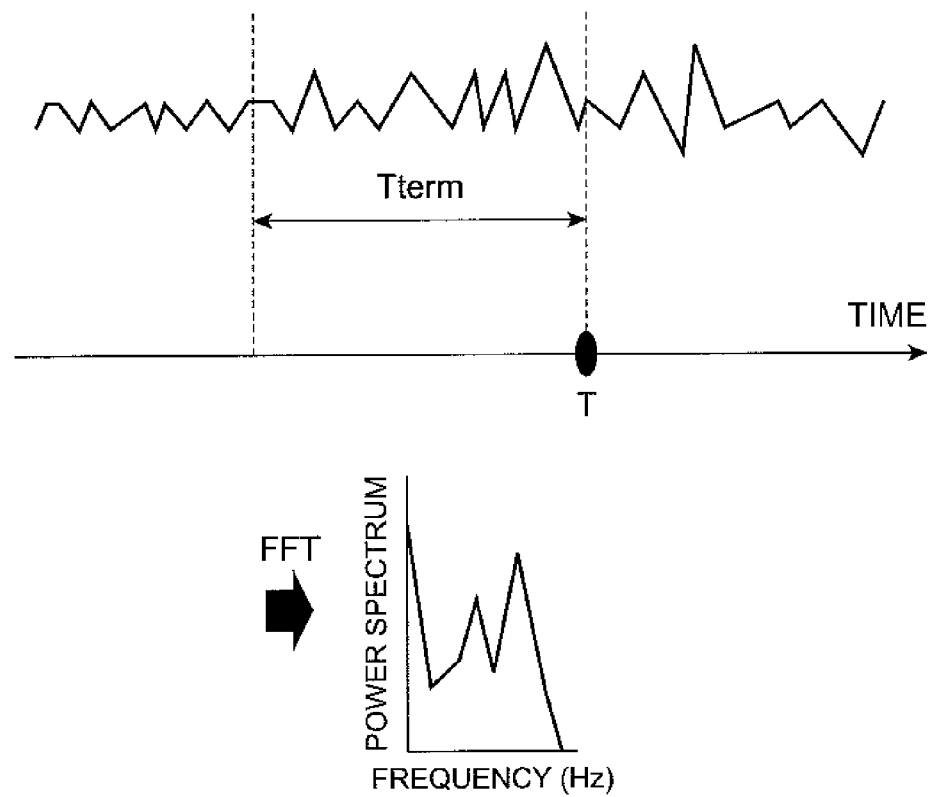
FIG. 12 is a waveform chart showing an example of a waveform obtained by performing FFT processing on a periodic time series of a pulse rate.

Subsequently, a pulse fluctuation is extracted as another pulse feature value of the driver (step S13). Specifically, regarding the time-series data (refer to FIG. 11) of the pulse period, as shown in FIG. 12, fast Fourier transform (FFT) is performed on the analysis unit section width $T_{term}$ before the reference time T (arbitrary time stamp) so that a power (amplitude) spectrum over a frequency component is acquired.

Figure 13:
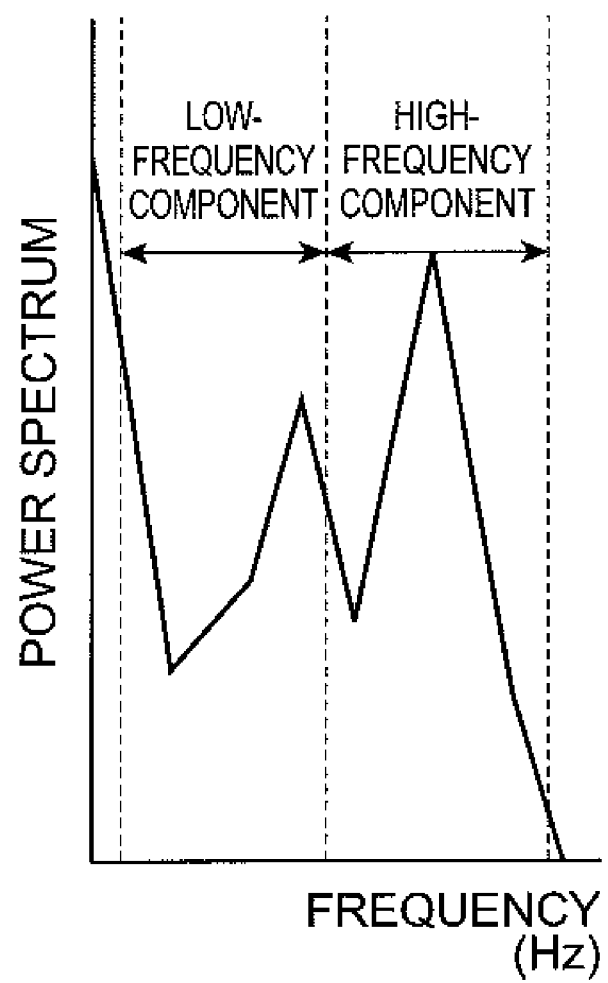
FIG. 13 is a waveform chart showing a state where two frequency bands are set for a waveform obtained by performing FFT processing.

Then, as shown in FIG. 13, two frequency bands (a low-frequency component and a high frequency component) are set for the power spectrum obtained for every analysis unit section width $T_{term}$ by fast Fourier transform. These frequency bands are bands where a pulse fluctuation (change) appears easily. In addition, the amplitude spectrum is integrated for each frequency band.

Figure 14:
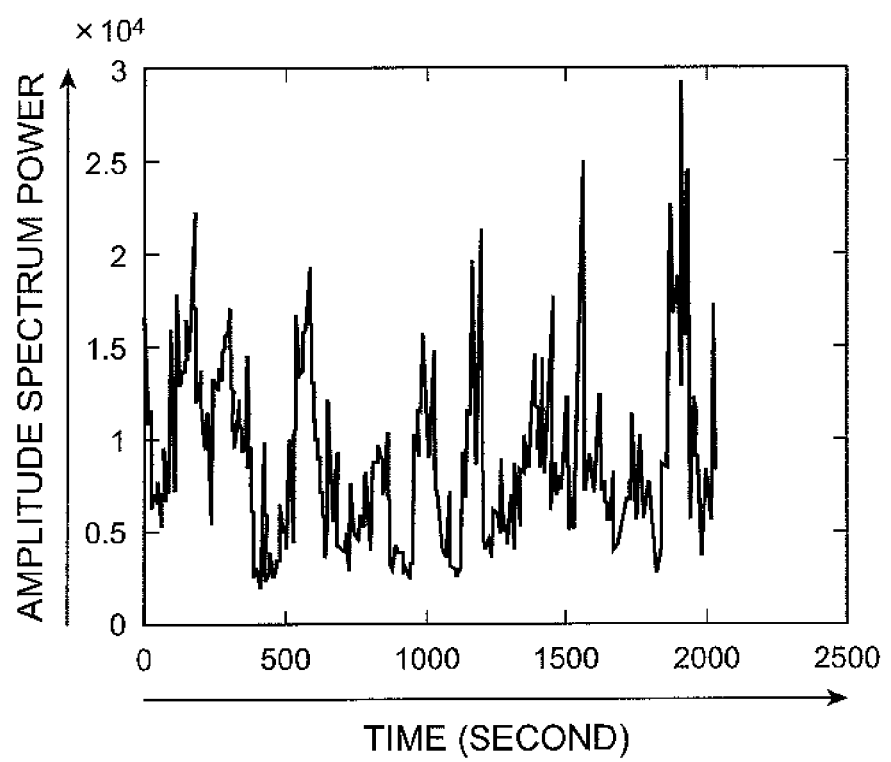
FIG. 14 is a waveform chart showing an example of a periodic time series of a pulse fluctuation.

By repeatedly performing the fast Fourier transform processing, the setting processing of a frequency band, and the integration processing, the time-series data of the amplitude spectrum power for each frequency band is acquired, as shown in FIG. 14. The time-series data of the amplitude spectrum power is time-series data of the pulse fluctuation. As a result, a pulse fluctuation low-frequency component value indicating the movement of the sympathetic nerve and a pulse fluctuation high-frequency component value indicating the movement of the parasympathetic nerve are acquired. In addition, the ratio (pulse fluctuation ratio value) of the pulse fluctuation low-frequency component value and the pulse fluctuation high-frequency component value is acquired by dividing the pulse fluctuation low-frequency component value by the pulse fluctuation high-frequency component value.

Then, the reference section width (reference time width) of the pulse feature value referred to in order to acquire the standard deviation of the pulse feature value is set (step S14). Setting of the reference section width is performed for each of the value of the pulse rate, the pulse fluctuation low-frequency component value, the pulse fluctuation high-frequency component value, and the pulse fluctuation ratio value. The case where a specific technique of setting the reference section width is performed for the value of the pulse rate will be described below as an example.

Figure 15:
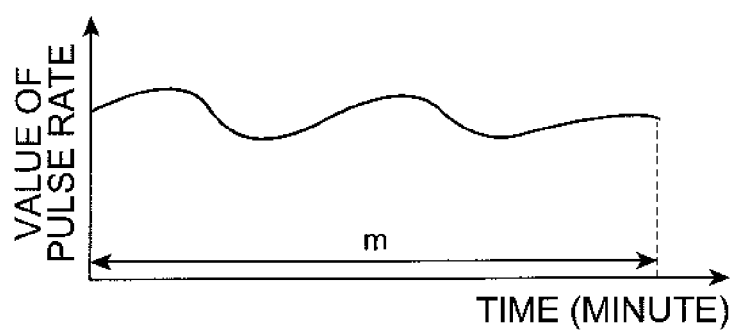
FIG. 15 is a waveform chart showing a method of setting the reference section width of the pulse feature value.
Figure 15:
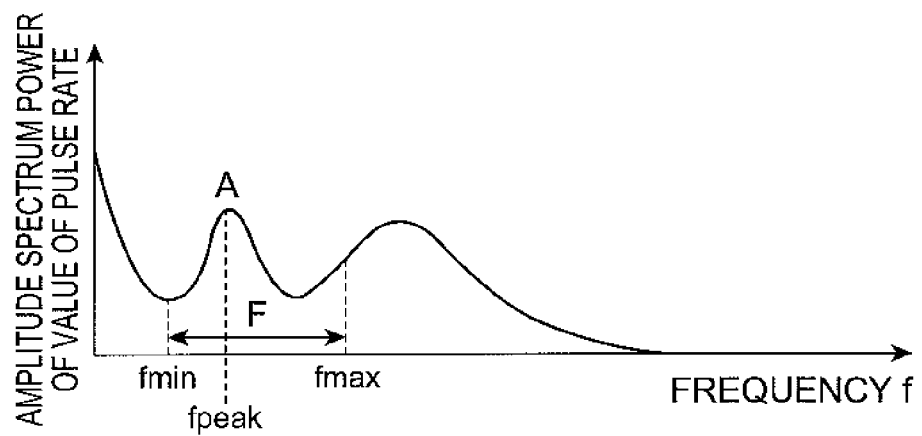

That is, first, as shown in FIG. 15A, the time-series data (refer to FIG. 11) of the value of the pulse rate is divided for every arbitrary length (about several minutes) m and it is stored in a data storage buffer for reference time width determination.

Then, a frequency analysis result shown in FIG. 15B is acquired by performing a fast Fourier transform (FFT) operation on the value of the pulse rate stored in the data storage buffer. Here, F is a frequency range, $f_{max}$ is a maximum value of the frequency range F, $f_{min}$ is a minimum value of the frequency range F, A is a maximum value of the amplitude spectrum power of the value of the pulse rate in the frequency range F, and $f_{peak}$ is a frequency which becomes the maximum value A of the amplitude spectrum power. The frequency range F is a range obtained by statistical analyses which corresponds to the drowsiness of each person, and the frequency $f_{peak}$ is a frequency at which a change of drowsiness particularly tends to occur among the values of the pulse rates.

Then, the reference section width of the value of the pulse rate is calculated from the following calculation expression using such a frequency $f_{peak}$ Reference section width of a value of the pulse rate=1/$f_{peak}$ By extracting the peak frequency $f_{peak}$ in the frequency range F as a place where drowsiness noticeably occurs as described above, an effect of data noise is removed to determine a drowsy state (described later).

Then, the value of the pulse rate, the pulse fluctuation low-frequency component value, the pulse fluctuation high-frequency component value, and the pulse fluctuation ratio value are cut by the reference section width (the total number of data items: N), and the average value in this section is calculated (step S15).

Cut value of the pulse rate=$\{X_1, X_2, X_3, \ldots, X_N\}$

Cut pulse fluctuation low-frequency component value=$\{Y_1, Y_2, Y_3, \ldots, Y_N\}$ Cut pulse fluctuation high-frequency component value=$\{Z_1, Z_2, Z_3, \ldots, Z_N\}$ Cut pulse fluctuation ratio value=$\{W_1, W_2, W_3, \ldots, W_N\}$ Then, in the same manner as described above, each of the value of the pulse rate, the pulse fluctuation low-frequency component value, the pulse fluctuation high-frequency component value, and the pulse fluctuation ratio value is cut by the reference section width, and the standard deviation value in this section is calculated (step S16).

A calculation expression of the standard deviation of the value of the pulse rate is as follows.

$$\text{Standard deviation of value of pulse rate} = \sqrt{\frac{1}{N-1}\sum_{i=1}^{N}(X_i - X_{ave})^2} \quad \text{[Expression 2]}$$

N: The total number of cut pulse rate value data items
i: Number of pulse rate value
$X_i$: i-th value of the pulse rate
$X_{ave}$: Average value of N value of the pulse rates A calculation expression of the standard deviation of the pulse fluctuation low-frequency component value is as follows.

$$\text{Standard deviation of pulse fluctuation low-frequency component value} = \sqrt{\frac{1}{N-1}\sum_{i=1}^{N}(Y_i - Y_{ave})^2} \quad \text{[Expression 3]}$$

N: The total number of cut pulse fluctuation low-frequency component value data items
i: Number of pulse fluctuation low-frequency component value
$Y_i$: i-th pulse fluctuation low-frequency component value
$Y_{ave}$: Average value of N pulse fluctuation low-frequency component values A calculation expression of the standard deviation of the pulse fluctuation high-frequency component value is as follows.

$$\text{Standard deviation of pulse fluctuation high-frequency component value} = \sqrt{\frac{1}{N-1}\sum_{i=1}^{N}(Z_i - Z_{ave})^2} \quad \text{[Expression 4]}$$

N: The total number of cut pulse fluctuation high-frequency component value data items
i: Number of pulse fluctuation high-frequency component value
$Z_i$: i-th pulse fluctuation high-frequency component value
$Z_{ave}$: Average value of N pulse fluctuation high-frequency component values A calculation expression of the standard deviation of the pulse fluctuation ratio value is as follows.

$$\text{Standard deviation of pulse fluctuation ratio value} = \sqrt{\frac{1}{N-1}\sum_{i=1}^{N}(W_i - W_{ave})^2} \quad \text{[Expression 5]}$$

N: The total number of cut pulse fluctuation ratio value data items
i: Number of pulse fluctuation ratio value
$W_i$: i-th pulse fluctuation ratio value
$W_{ave}$: Average value of N pulse fluctuation ratio values Subsequently, the standard deviation values of the value of the pulse rate, the pulse fluctuation low-frequency component value, the pulse fluctuation high-frequency component value, and the pulse fluctuation ratio value are corrected (step S17). The correction of these standard deviation values is performed as follows.

That is, first, the pulse rate standard deviation value, the pulse fluctuation low-frequency component standard deviation value, the pulse fluctuation high-frequency component standard deviation value, and the pulse fluctuation ratio standard deviation value, which were acquired in step S16, and a value of the pulse rate, a pulse fluctuation low-frequency component value, a pulse fluctuation high-frequency component value, and a pulse fluctuation ratio value, which are used for correction, are stored in a buffer which stores standard deviation values to be corrected.

Here, the data acquired in a state where there is no drowsiness (for example, at the start of driving) is used as the value of the pulse rate, the pulse fluctuation low-frequency component value, the pulse fluctuation high-frequency component value, and the pulse fluctuation ratio value which are stored in the buffer which stores standard deviation values to be corrected. These data items may be acquired before driving starts or may be acquired in advance and stored in a memory of the drowsiness detection ECU 3, for example.

Examples of the pulse rate standard deviation value and the value of the pulse rate, which are stored in the buffer which stores standard deviation values to be corrected, are shown in FIG. 16A.

Then, the pulse rate standard deviation value, the pulse fluctuation low-frequency component standard deviation value, the pulse fluctuation high-frequency component standard deviation value, and the pulse fluctuation ratio standard deviation value are corrected using the following calculation expression, thereby acquiring a corrected pulse rate standard deviation value, a corrected pulse fluctuation low-frequency component standard deviation value, a corrected pulse fluctuation high-frequency component standard deviation value, and a corrected pulse fluctuation ratio standard deviation value.

Corrected pulse rate standard deviation value=pulse rate standard deviation value/value of pulse rate Corrected pulse fluctuation low-frequency component standard deviation value=pulse fluctuation low-frequency component standard deviation value/pulse fluctuation low-frequency component value Corrected pulse fluctuation high-frequency component standard deviation value=pulse fluctuation high-frequency component standard deviation value/pulse fluctuation high-frequency component value Corrected pulse fluctuation ratio standard deviation value=pulse fluctuation ratio standard deviation value/pulse fluctuation ratio value [Expression 6]

The corrected pulse rate standard deviation value calculated from the pulse rate standard deviation value and the value of the pulse rate shown in FIG. 16A is shown in FIG. 16B.

Since the value of the pulse rate or the pulse rate standard deviation value varies from person to person, the determination result may differ depending on a subject if the pulse rate standard deviation value is used for drowsiness determination (described later) as it is. Accordingly, by correcting the pulse rate standard deviation value for every subject, the influence of a variation in the value of the pulse rate of each subject on the drowsiness determination result is eliminated. The same is true for the pulse fluctuation low-frequency component value, the pulse fluctuation high-frequency component value, and the pulse fluctuation ratio value.

Then, it is determined whether or not the driver is lightly drowsy using the corrected pulse rate standard deviation value, the corrected pulse fluctuation low-frequency component standard deviation value, the corrected pulse fluctuation high-frequency component standard deviation value, and the corrected pulse fluctuation ratio standard deviation value (step S18).

Figure 17:
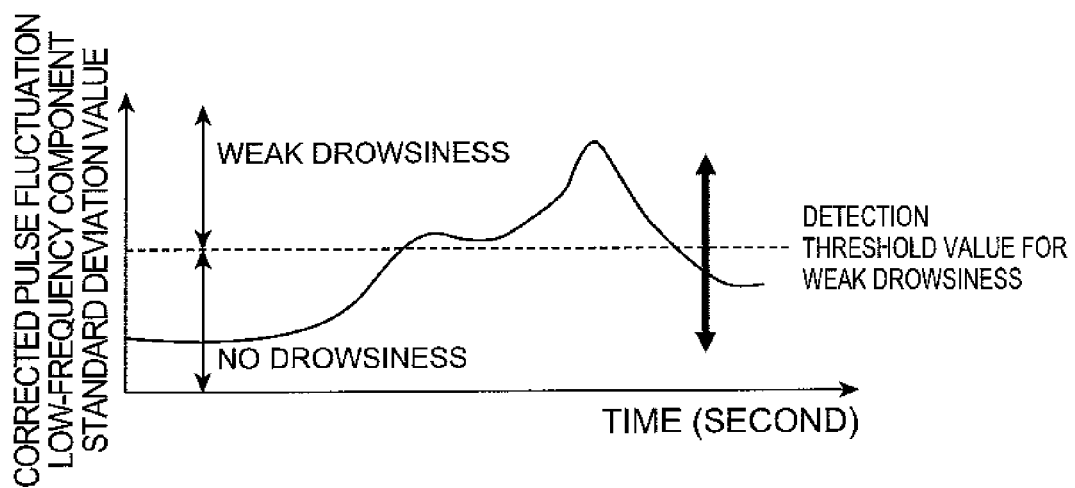
FIG. 17 is a waveform chart showing a method of determining drowsiness with a corrected pulse fluctuation low-frequency component standard deviation value.

An example of a method of determining drowsiness with the corrected pulse fluctuation low-frequency component standard deviation value is shown in FIG. 17. In the method shown in this drawing, the corrected pulse fluctuation low-frequency component standard deviation value is compared with a detection threshold value for light drowsiness set in advance. When the corrected pulse fluctuation low-frequency component standard deviation value is higher than the detection threshold value for light drowsiness, it is determined to be a state where there is light drowsiness. When the corrected pulse fluctuation low-frequency component standard deviation value is lower than the detection threshold value for light drowsiness, it is determined to be a state where there is no drowsiness.

Moreover, also in the cases where the corrected pulse rate standard deviation value, the corrected pulse fluctuation high-frequency component standard deviation value, and the corrected pulse fluctuation ratio standard deviation value are used, it is similarly determined whether or not there is light drowsiness.

Figure 18:
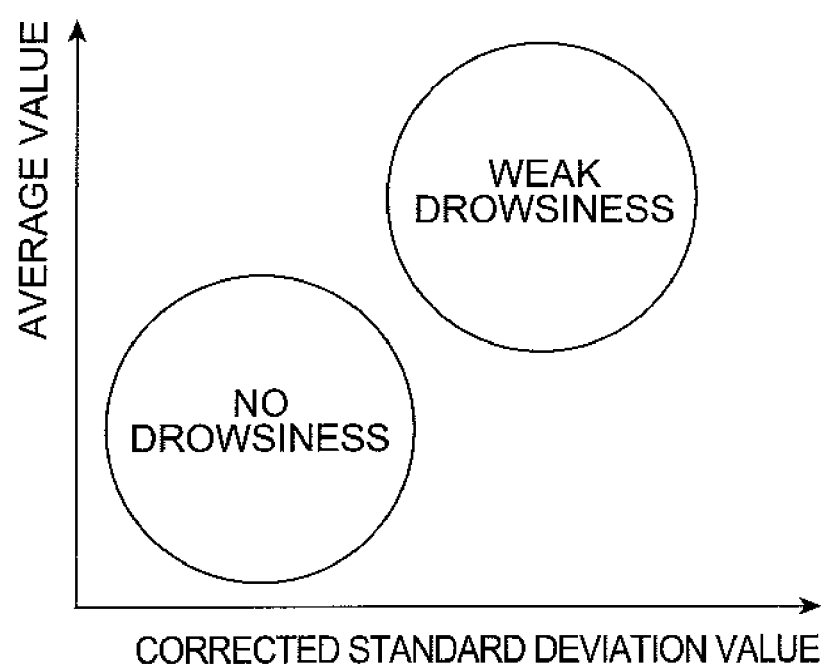
FIG. 18 is a conceptual view showing a method of determining drowsiness using two-dimensional coordinates of the corrected standard deviation value and the average value of the pulse feature values.

Another method of determining drowsiness is shown in FIG. 18. In the method shown in this drawing, it is determined in a two-dimensional manner whether or not there is light drowsiness using the corrected standard deviation value and the average value of the pulse feature values together.

Specifically, the data of the corrected standard deviation value and the average value of the pulse feature values are expressed in two-dimensional coordinates, and the drowsiness level is determined from the data distribution acquired at that time. When the data of both the corrected standard deviation value and the average value gathers at the large side, it is determined to be a state where there is light drowsiness. When the data of both the corrected standard deviation value and the average value gathers at the small side, it is determined to be a state where there is no drowsiness.

Figure 19:
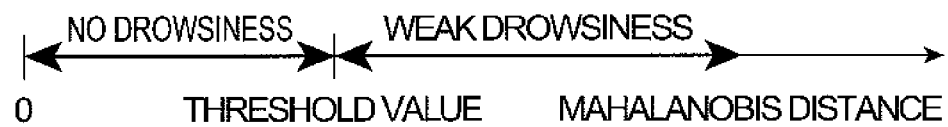
FIG. 19 is a conceptual view showing a method of determining drowsiness using the Mahalanobis-Taguchi method.

Still another method of determining drowsiness is shown in FIG. 19. In the method shown in this drawing, it is determined in a one-dimensional manner whether or not there is light drowsiness by a Mahalanobis-Taguchi method using the corrected standard deviation value and the average value of the pulse feature values together.

Specifically, the Mahalanobis distance is calculated on the basis of the corrected standard deviation value and the average value of the pulse feature values. In addition, when the Mahalanobis distance is higher than the detection threshold value for light drowsiness set in advance, it is determined to be a state where there is light drowsiness. When the Mahalanobis distance is lower than the detection threshold value for light drowsiness set in advance, it is determined to be a state where there is no drowsiness.

When it is determined that there is no drowsiness by the above-described method in step S18, the process returns to step S11 to repeatedly execute the processing in steps S11 to S18. On the other hand, when it is determined that there is light drowsiness in step S18, the occurrence of drowsiness is notified to the driver by controlling the alarm 4 (step S19), and then the process returns to step S11.

In the above, steps S11 to S13 shown in FIG. 8 form a pulse feature value extracting means for extracting the pulse feature value from the heartbeat or a pulse measured by a measurement means 2. Steps S16 and S17 form a variation distribution calculating means for calculating the variation distribution of the pulse feature value extracted by the pulse feature value extracting means. Step S18 forms a drowsiness level determining means for determining the drowsiness level of a subject using the variation distribution of the pulse feature value calculated by the variation distribution calculating means.

In addition, step S15 forms an average value calculating means for calculating the average value of the pulse feature values extracted by the pulse feature value extracting means. Step S14 forms a reference time width setting means for setting the reference time width of the pulse feature value referred to in order to acquire the standard deviation of the pulse feature value.

As described above, in the present embodiment, attention is paid to a pulse influenced by autonomic nerve activity relevant to the occurrence of drowsiness, a heartbeat or a pulse of a driver is measured to extract the pulse rate and a pulse fluctuation, standard deviations (variations) of these pulse rates and pulse fluctuations are calculated, and a determination regarding drowsiness of the driver is performed from the standard deviation or both the standard deviation and the average value. At this time, the drowsiness level of the driver can be determined as an index of a physiological state when driving while feeling light drowsiness of resisting drowsiness and trying to return to an alert state. In this case, light drowsiness of a driver can be detected with high precision regardless of the driver. Therefore, drowsy driving can be effectively prevented by demanding that the driver recover normal consciousness or take a rest when there is light drowsiness.

In addition, the present embodiment is not limited to the above-described. For example, in the present embodiment, a determination regarding drowsiness of a driver is performed using four pulse feature values called the value of the pulse rate, the pulse fluctuation low-frequency component value, the pulse fluctuation high-frequency component value, and the pulse fluctuation ratio value. However, it is also possible to use at least one of these four pulse feature values.

In addition, in the present embodiment, determination regarding drowsiness of a driver is performed by calculating the standard deviation of the pulse feature value. However, a standard error or the like may also be used instead of the standard deviation as long as it is based on the distribution of variations in the pulse feature value.

In addition, although the drowsiness detector 1 of the present embodiment is mounted in a vehicle, it may also be applied to those which detect the drowsiness level of a subject other than a driver of a vehicle.

[Second Embodiment]

Figure 20:
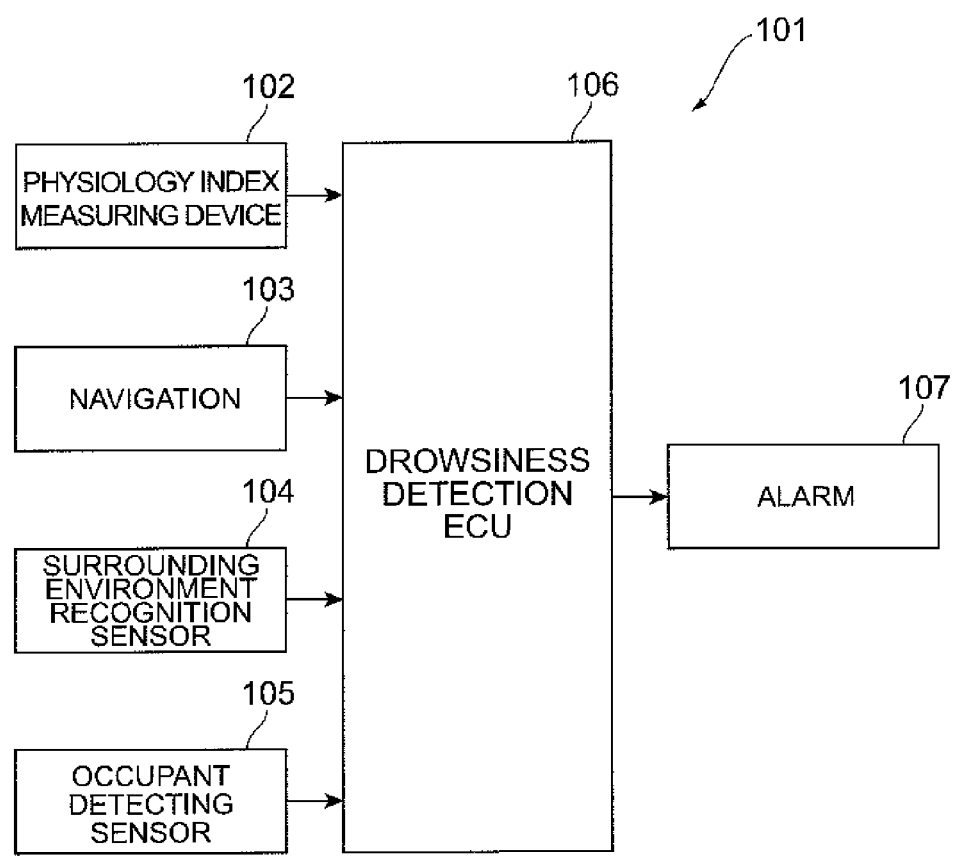
FIG. 20 is a block diagram showing the schematic configuration of a second embodiment of the drowsiness detector related to the present invention.

FIG. 20 is a block diagram showing the schematic configuration of a second embodiment of the drowsiness detector related to the present invention. In this drawing, a dzrowsiness detector 101 of the present embodiment is a device which is mounted in a vehicle and detects drowsiness of a driver of the vehicle. The drowsiness detector 101 includes a physiological index measuring device 102, a navigation device 103, a surrounding environment recognition sensor 104, an occupant detecting sensor 105, a drowsiness detection ECU (Electronic Control Unit) 106, and an alarm 107.

The physiological index measuring device 102 is a device which measures a physiological index of a driver. Specifically, for example, an electrocardiogram system which measures a heartbeat and a plethysmograph which measures a pulse from the fingertip or forearm may be mentioned as the physiological index measuring device 102.

The navigation device 103 is a device which detects the current position of the vehicle using a GPS (global positioning system) or which acquires the information regarding a road, on which the vehicle travels, from the road map information stored in the internal memory.

The surrounding environment recognition sensor 104 is a sensor which recognizes whether or not there are moving objects, such as other vehicles, pedestrians, and bicycles, in the vicinity of the vehicle. An image sensor, such as a camera, a radar sensor, an ultrasonic sensor, a device for communication between vehicles which receives other vehicle information by performing wireless communications with other vehicles, and the like are used as the surrounding environment recognition sensor 104.

The occupant detecting sensor 105 is a sensor which detects whether or not there is a passenger and whether or not a driver is moving. An image sensor, such as a camera, a contact sensor which detects an operation state of the navigation device 103 or the like, and the like are used as the occupant detecting sensor 105.

The drowsiness detection ECU 106 is configured to include a CPU, memories such as a ROM or a RAM, and an input and output circuit. The drowsiness detection ECU 106 is input with the output data (measurement data) of the physiological index measuring device 102, the information of the navigation device 103, the output data of the surrounding environment recognition sensor 104 and the occupant detecting sensor 105, performs predetermined processing, and determines whether or not a driver is in a lightly drowsy state.

The alarm 107 is a device which notifies a driver of the occurrence of drowsiness by giving an alarm with a sound (buzzing sound), an image (screen display), vibration (vibrator), or the like.

Figure 21:
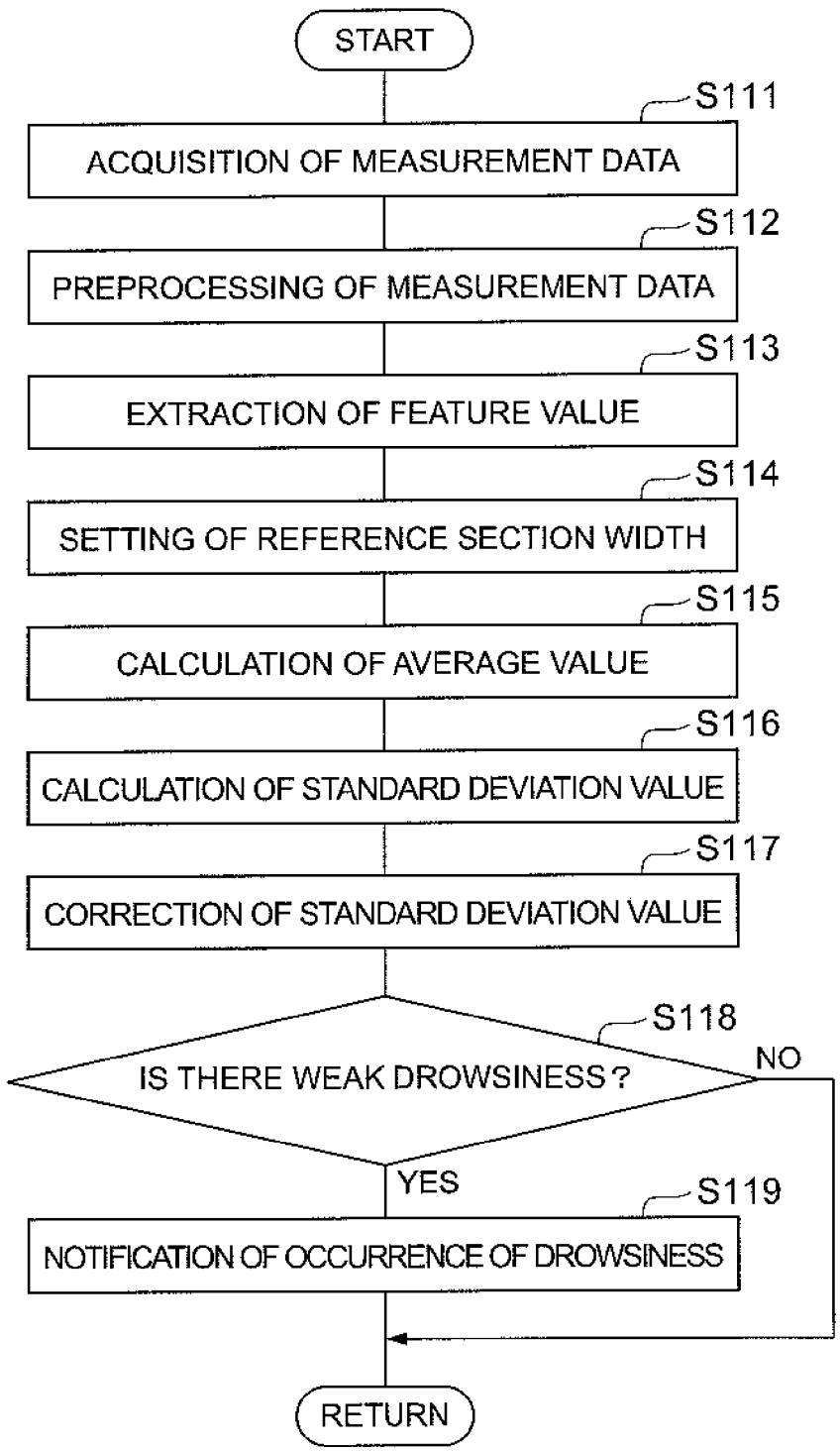
FIG. 21 is a flow chart showing the details of the procedure of drowsiness detection processing executed by a drowsiness detection ECU shown in FIG. 20.

FIG. 21 is a flow chart showing the details of the procedure of drowsiness detection processing executed by the drowsiness detection ECU 106. Here, the case of measuring a pulse of a driver with an electrocardiogram system as the physiological index measuring device 102 will be described as an example.

In this drawing, the measurement data (raw pulse data) of the physiological index measuring device 102 is acquired first (step S111), and the measurement data is preprocessed (step S112). Specifically, first, components in a predetermined pass band (for example, 0.1 Hz to 30 Hz) are extracted by performing band pass filter (BPF) processing on the raw pulse data in order to remove noise of the pulse data.

Figure 22:
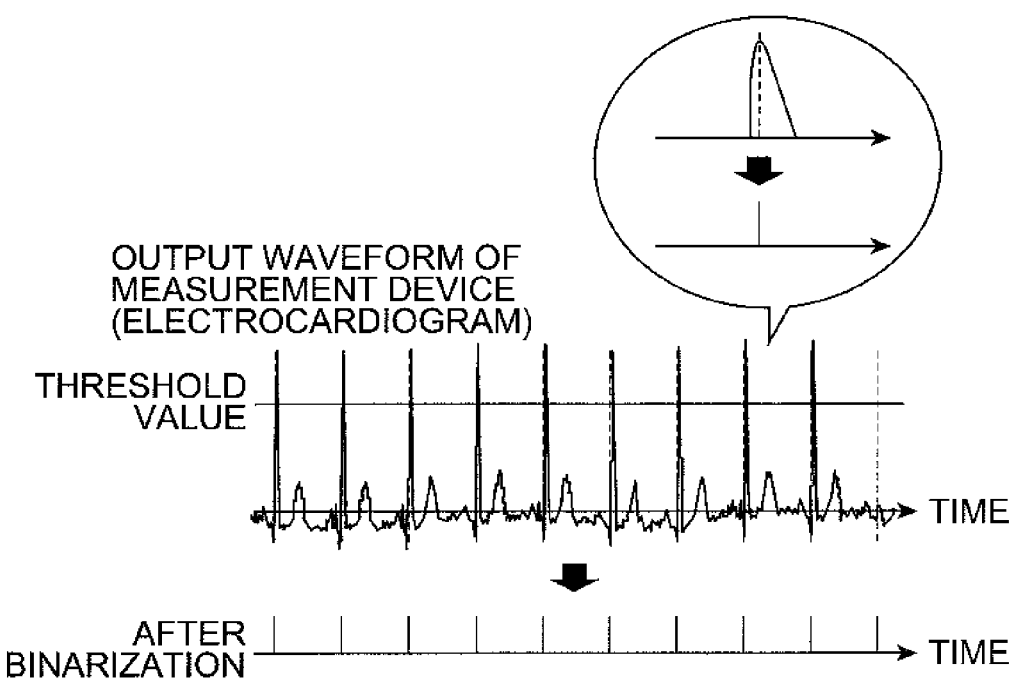
FIG. 22 is a waveform chart showing an example of an output waveform of a physiological index measuring device shown in FIG. 20 and a binarized waveform.

Then, as shown in FIG. 22, the waveform of the pulse data obtained by performing BPF processing is binarized by comparing it with the threshold value set in advance. At this time, the binarization is performed so that it becomes "1" at a timing when each R-wave portion of the waveform of the pulse data is a maximum (refer to the enlarged view in FIG. 22).

Figure 23:
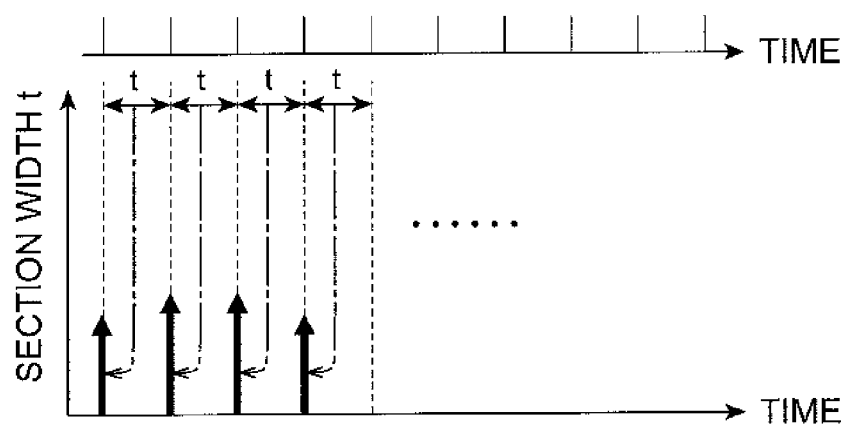
FIG. 23 is a waveform chart showing an example of the section width and a periodic time series of a binarized waveform.
Figure 23:
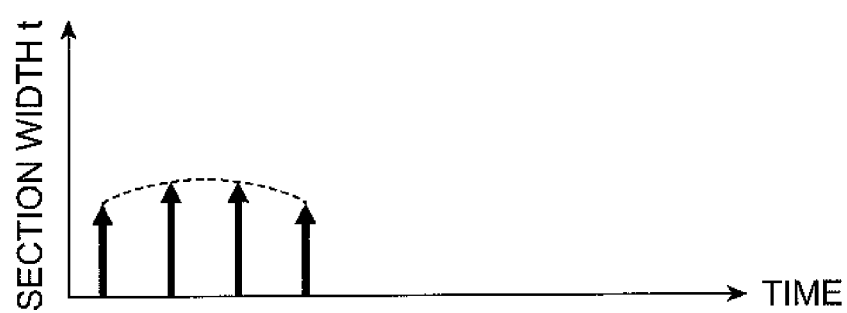

Then, as shown in FIG. 23A, a section width (time interval) t is calculated at each timing when the binary data it becomes "1", and a graph having each section width t as a vertical axis is generated. At this time, the section width t is equivalent to a pulse period of a driver.

Figure 24:
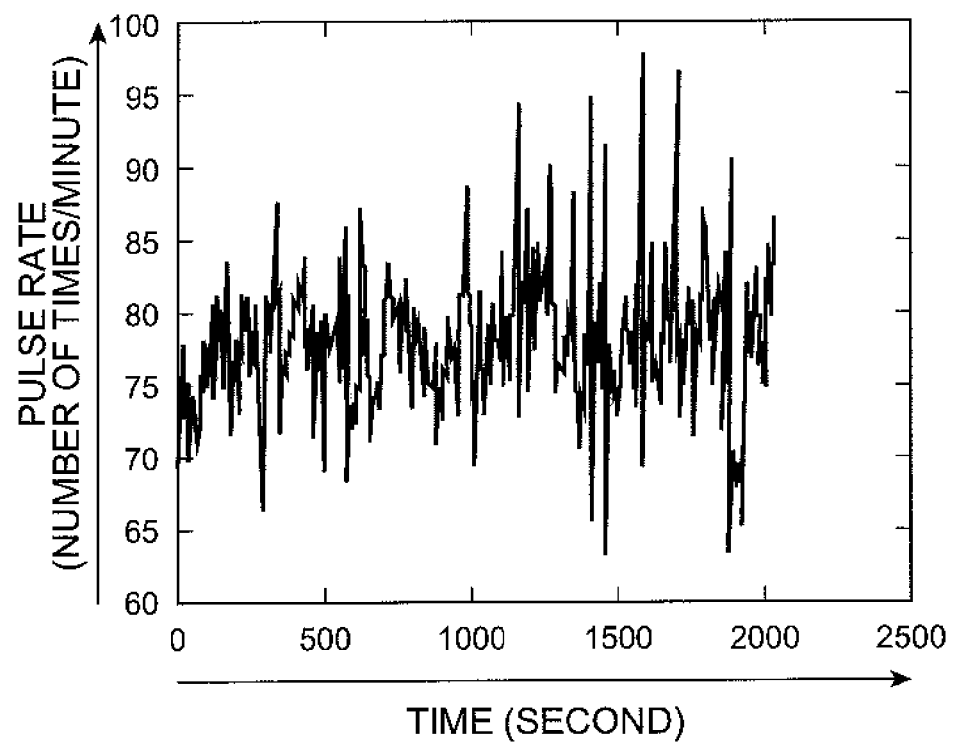
FIG. 24 is a waveform chart showing an example of a periodic time series of a pulse rate.

Then, as shown in FIG. 23B, a curve (refer to the broken line) of the pulse period is obtained by interpolating the graph of the pulse period, and the time-series data of the pulse period is acquired. Then, as shown in FIG. 24, the vertical axis unit of the time-series data of the pulse period is converted into the pulse rate per minute, for example. Accordingly, the value of the pulse rate of the driver can be acquired as one of the pulse feature values.

Figure 25:
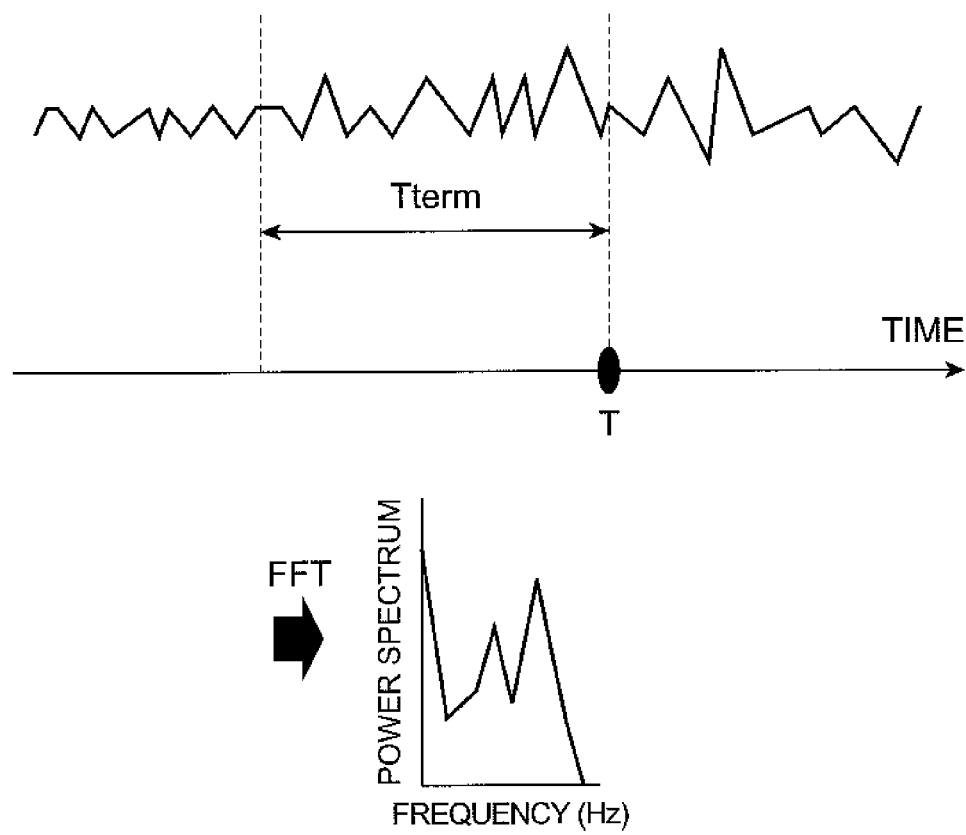
FIG. 25 is a waveform chart showing an example of a waveform obtained by performing FFT processing on a periodic time series of a pulse rate.

Subsequently, a pulse fluctuation is extracted as another pulse feature value of the driver (step S113). Specifically, regarding the time-series data (refer to FIG. 24) of the pulse period, as shown in FIG. 25, fast Fourier transform (FFT) is performed on the analysis unit section width $T_{term}$ before the reference time T (arbitrary time stamp) so that a power (amplitude) spectrum over a frequency component is acquired.

Figure 26:
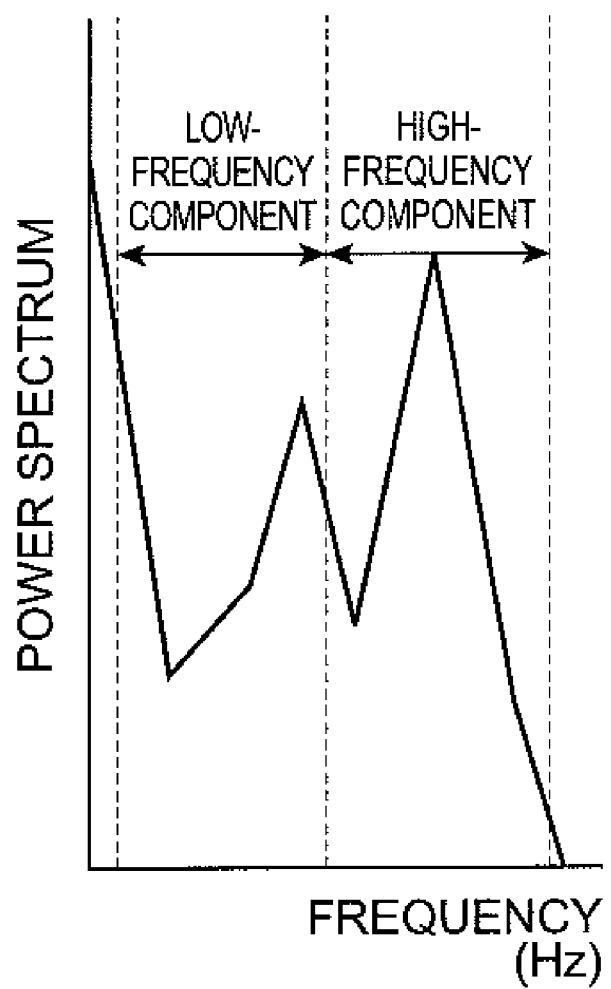
FIG. 26 is a waveform chart showing a state where two frequency bands are set for a waveform obtained by performing FFT processing.

Then, as shown in FIG. 26, two frequency bands (a low-frequency component and a high frequency component) are set for the power spectrum obtained for every analysis unit section width $T_{term}$ by fast Fourier transform. These frequency bands are bands where a pulse fluctuation (change) appears easily. In addition, the amplitude spectrum is integrated for each frequency band.

Figure 27:
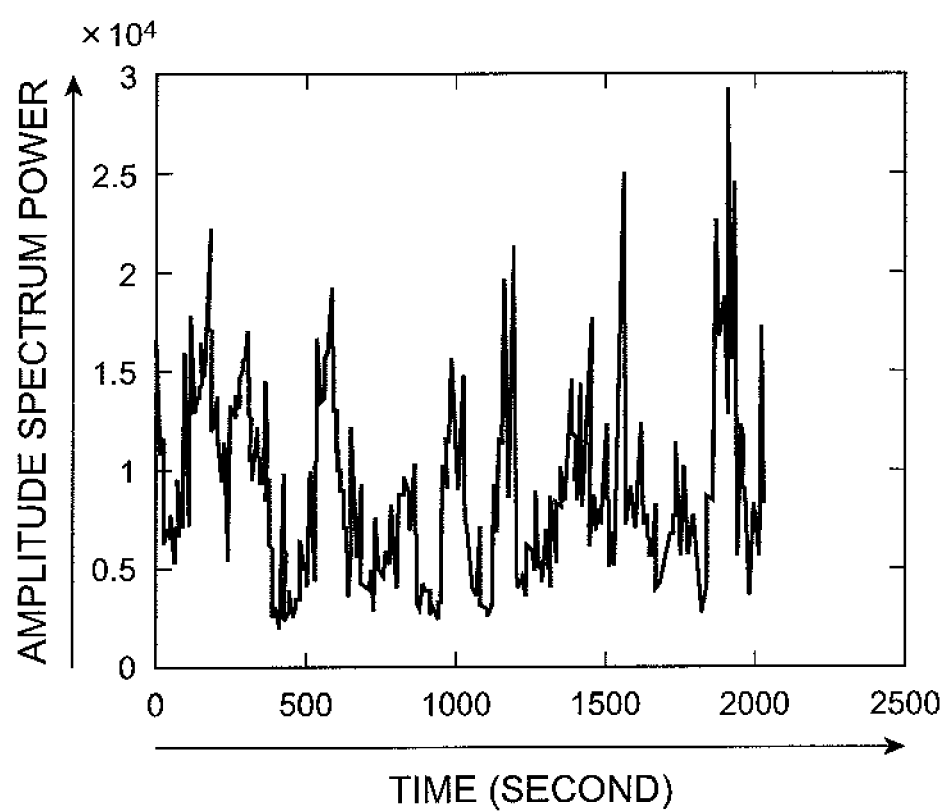
FIG. 27 is a waveform chart showing an example of a periodic time series of a pulse fluctuation.

By repeatedly performing the fast Fourier transform processing, the setting processing of a frequency band, and the integration processing, the time-series data of the amplitude spectrum power for each frequency band is acquired, as shown in FIG. 27. The time-series data of the amplitude spectrum power is time-series data of the pulse fluctuation. As a result, a pulse fluctuation low-frequency component value indicating the movement of the sympathetic nerve and a pulse fluctuation high-frequency component value indicating the movement of the parasympathetic nerve are acquired. In addition, the ratio (pulse fluctuation ratio value) of the pulse fluctuation low-frequency component value and the pulse fluctuation high-frequency component value is acquired by dividing the pulse fluctuation low-frequency component value by the pulse fluctuation high-frequency component value.

Then, the reference section width (reference time width) of the pulse feature value referred to in order to acquire the standard deviation of the pulse feature value is set (step S114). Setting of the reference section width is performed for each of the value of the pulse rate, the pulse fluctuation low-frequency component value, the pulse fluctuation high-frequency component value, and the pulse fluctuation ratio value. The case where a specific technique of setting the reference section width is performed for the value of the pulse rate will be described below as an example.

Figure 28:
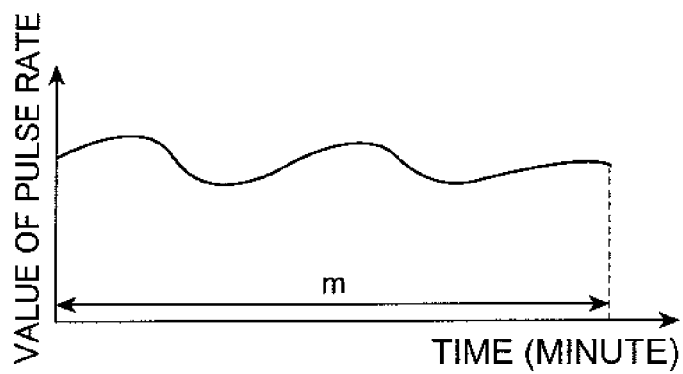
FIG. 28 is a waveform chart showing a method of setting the reference section width of the pulse feature value.
Figure 28:
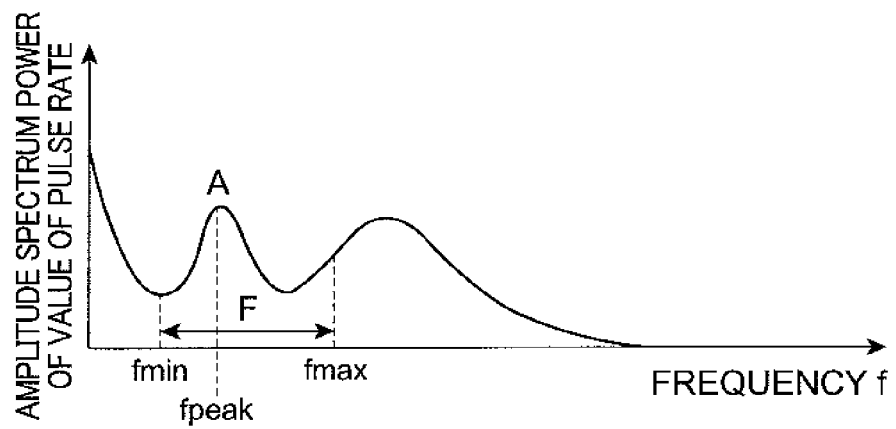

That is, first, as shown in FIG. 28A, the time-series data (refer to FIG. 24) of the value of the pulse rate is divided for every arbitrary length (about several minutes) m and it is stored in a data storage buffer for reference time width determination.

Then, a frequency analysis result shown in FIG. 28B is acquired by performing a fast Fourier transform (FFT) operation on the value of the pulse rate stored in the data storage buffer. Here, F is a frequency range, $f_{max}$ is a maximum value of the frequency range F, $f_{min}$ is a minimum value of the frequency range F, A is a maximum value of the amplitude spectrum power of the value of the pulse rate in the frequency range F, and $f_{peak}$ is a frequency which becomes the maximum value A of the amplitude spectrum power. The frequency range F is a range obtained by statistical analyses which corresponds to the drowsiness of each person, and the frequency $f_{peak}$ is a frequency at which a change of drowsiness particularly tends to occur among the value of the pulse rates.

Then, the reference section width of the value of the pulse rate is calculated from the following calculation expression using such a frequency $f_{peak}$.

Reference section width of a value of the pulse rate=1/$f_{peak}$

By extracting the peak frequency $f_{peak}$ in the frequency range F as a place where drowsiness noticeably occurs as described above, an effect of data noise is removed to determine a drowsy state (described later).

Then, the value of the pulse rate, the pulse fluctuation low-frequency component value, the pulse fluctuation high-frequency component value, and the pulse fluctuation ratio value are cut by the reference section width (the total number of data items: N), and the average value in this section is calculated (step S115).

Cut value of the pulse rate=$\{X_1, X_2, X_3, \ldots, X_N\}$

Cut pulse fluctuation low-frequency component value=$\{Y_1, Y_2, Y_3, \ldots, Y_N\}$ Cut pulse fluctuation high-frequency component value=$\{Z_1, Z_2, Z_3, \ldots, Z_N\}$ Cut pulse fluctuation ratio value=$\{W_1, W_2, W_3, \ldots, W_N\}$ Then, in the same manner as described above, each of the value of the pulse rate, the pulse fluctuation low-frequency component value, the pulse fluctuation high-frequency component value, and the pulse fluctuation ratio value is cut by the reference section width, and the standard deviation values of the value of the pulse rate, the pulse fluctuation low-frequency component value, the pulse fluctuation high-frequency component value, and the pulse fluctuation ratio value in this section are calculated by the calculation expressions shown in the above expressions 2 to 5 (step S116).

Subsequently, the standard deviation values of the value of the pulse rate, the pulse fluctuation low-frequency component value, the pulse fluctuation high-frequency component value, and the pulse fluctuation ratio value are corrected (step S117). A functional block for executing the processing in this step S117 is shown in FIG. 29.

Figure 29:
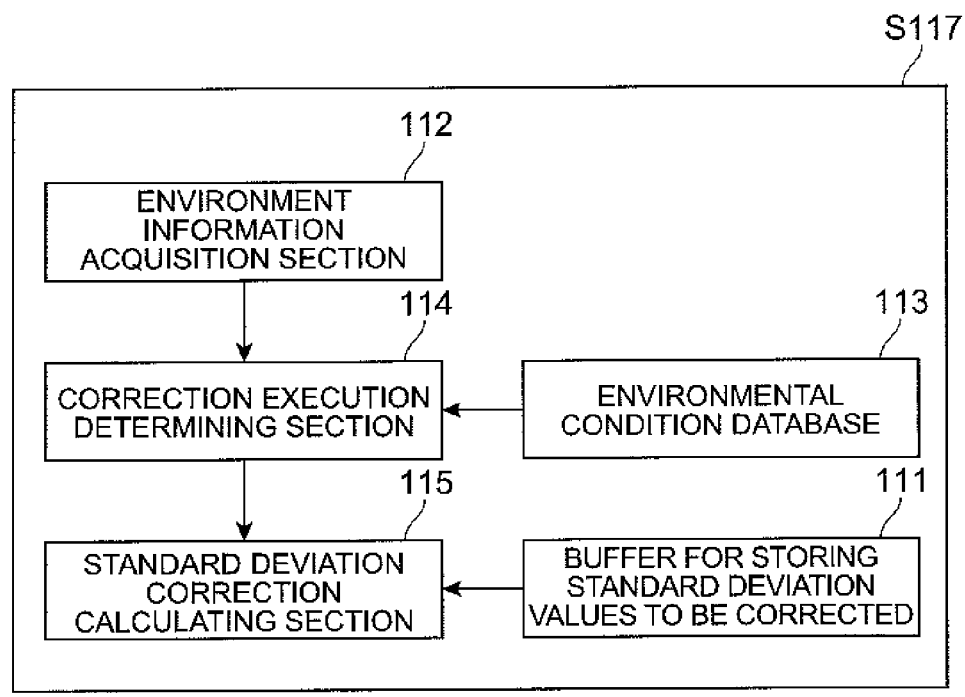
FIG. 29 is a view showing a functional block which executes standard deviation value correction processing shown in FIG. 21.

In FIG. 29, there are a buffer for storing standard deviation values to be corrected 111, an environment information acquisition section 112, an environmental condition database 113, a correction execution determining section 114, and a standard deviation correction calculating section 115 as functions for correcting the standard deviation values of the value of the pulse rate, the pulse fluctuation low-frequency component value, the pulse fluctuation high-frequency component value, and the pulse fluctuation ratio value.

The buffer for storing standard deviation values to be corrected 111 stores pulse feature value standard deviation values to be corrected and instantaneous values (pulse feature value at the current time) used for correction. The pulse feature value standard deviation values are the pulse rate standard deviation value, the pulse fluctuation low-frequency component standard deviation value, the pulse fluctuation high-frequency component standard deviation value, and the pulse fluctuation ratio standard deviation value acquired in step S116. The instantaneous values used for correction are the value of the pulse rate, the pulse fluctuation low-frequency component value, the pulse fluctuation high-frequency component value, and the pulse fluctuation ratio value at the current time.

The environment information acquisition section 112 acquires the information regarding the traveling environment of the vehicle on the basis of the information of the navigation device 103 and the output data of the surrounding environment recognition sensor 104 and the occupant detecting sensor 105. The information regarding a road on which a vehicle travels, the information regarding the surrounding environment of a vehicle, and the information regarding occupants including a driver are mentioned as the information regarding the traveling environment of the vehicle. The information regarding a road on which a vehicle travels is acquired from the navigation device 103, the information regarding the surrounding environment of a vehicle is acquired on the basis of the output data of the surrounding environment recognition sensor 104, and the information regarding the occupants is acquired on the basis of the output data of the occupant detecting sensor 105.

Environmental conditions in which the pulse feature value standard deviation value is not corrected are stored and held in the environmental condition database 113. The environmental conditions in which the pulse feature value standard deviation value is not corrected are environments where conscious attention tends to be stimulated, such as a condition in which a vehicle travels in any of an urban area, a curved road, a road along which the driver has not driven previously, and an intersection, a condition in which moving objects, such as other vehicles, pedestrians, and bicycles, are present in the vicinity of the vehicle, and a condition in which a passenger is in the vehicle and the driver is moving with a certain purpose.

The correction execution determining section 114 compares the information regarding the traveling environment of the vehicle acquired by the environment information acquisition section 112 with the environmental condition stored in the environmental condition database 113. When the information regarding the traveling environment of the vehicle matches the environmental condition stored in the environmental condition database 113, correction processing on the pulse feature value standard deviation value is not performed. That is, when the vehicle travels in any of an urban area, a curved road, a road along which the driver has not driven previously, and an intersection, when a moving object is present in the vicinity of the vehicle, and when a passenger is in the vehicle and the driver is moving, correction processing on the pulse feature value standard deviation value is not performed. On the other hand, when the information regarding the traveling environment of the vehicle does not match the environmental condition stored in the environmental condition database 113, correction processing on the pulse feature value standard deviation value is performed.

When the correction execution determining section 114 determines that the pulse feature value standard deviation value is to be corrected, the standard deviation correction calculating section 115 corrects the pulse rate standard deviation value, the pulse fluctuation low-frequency component standard deviation value, the pulse fluctuation high-frequency component standard deviation value, and the pulse fluctuation ratio standard deviation value using the calculation expression shown in the above expression 6, thereby acquiring a corrected pulse rate standard deviation value, a corrected pulse fluctuation low-frequency component standard deviation value, a corrected pulse fluctuation high-frequency component standard deviation value, and a corrected pulse fluctuation ratio standard deviation value.

Examples of the pulse rate standard deviation value and the value of the pulse rate, which are stored in the buffer for storing standard deviation values to be corrected 111, are shown in FIG. 30A. In this case, the corrected pulse rate standard deviation value calculated by the above expression is shown in FIG. 30B.

After returning to FIG. 21 to execute step S117 described above, it is determined whether or not the driver is lightly drowsy using the corrected pulse rate standard deviation value, the corrected pulse fluctuation low-frequency component standard deviation value, the corrected pulse fluctuation high-frequency component standard deviation value, and the corrected pulse fluctuation ratio standard deviation value (step S118).

Figure 31:
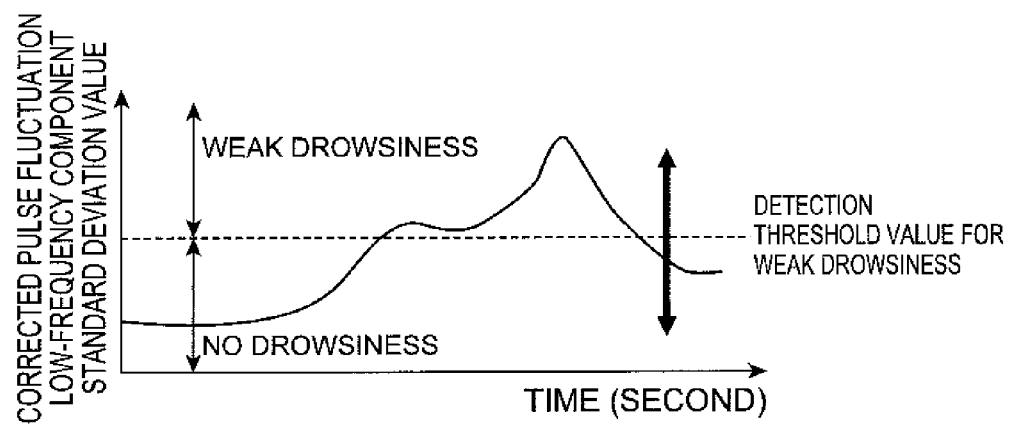
FIG. 31 is a waveform chart showing an example of a method of determining drowsiness with a corrected pulse fluctuation low-frequency component standard deviation value.

An example of a method of determining drowsiness with the corrected pulse fluctuation low-frequency component standard deviation value is shown in FIG. 31. In the method shown in this drawing, the corrected pulse fluctuation low-frequency component standard deviation value is compared with a detection threshold value for light drowsiness set in advance. When the corrected pulse fluctuation low-frequency component standard deviation value is higher than the detection threshold value for light drowsiness, it is determined to be a state where there is light drowsiness. When the corrected pulse fluctuation low-frequency component standard deviation value is lower than the detection threshold value for light drowsiness, it is determined to be a state where there is no drowsiness.

Moreover, also in the cases where the corrected pulse rate standard deviation value, the corrected pulse fluctuation high-frequency component standard deviation value, and the corrected pulse fluctuation ratio standard deviation value are used, it can be similarly determined whether or not there is light drowsiness.

When it is determined that there is no drowsiness by the above-described method in step S118, the process returns to step S111 to repeatedly execute the processing in steps S111 to S118. On the other hand, when it is determined that there is light drowsiness in step S118, the occurrence of drowsiness is notified to the driver by controlling the alarm 107 (step S119), and then the process returns to step S111.

The physiological index measuring device 102 forms a measurement means for measuring the heartbeat or a pulse of the driver. Steps S111 to S113 in the drowsiness detection ECU 106 form a pulse feature value extracting means for extracting the pulse feature value from the heartbeat or a pulse of the driver. Steps S114 to S116 form a standard deviation calculating means for calculating the standard deviation of the pulse feature value. The navigation device 103, the surrounding environment recognition sensor 104, the occupant detecting sensor 105, and the environment information acquisition section 112 of step S117 in the drowsiness detection ECU 106 form a traveling environment detecting means for detecting the traveling environment of a vehicle. The buffer for storing standard deviation values to be corrected 111, the environmental condition database 113, the correction execution determining section 114, and the standard deviation correction calculating section 115 of step S117 in the drowsiness detection ECU 106 form a correction means for correcting the standard deviation of the pulse feature value with the pulse feature value according to the traveling environment of a vehicle. Step S118 forms a drowsiness level determining means for determining the drowsiness level of the driver using the distribution of the standard deviation of the pulse feature value after correction acquired by the correction means.

As described above, in the present embodiment, attention is paid to a pulse influenced by autonomic nerve activity relevant to the occurrence of drowsiness, a heartbeat or a pulse of the driver is measured to extract the pulse rate and a pulse fluctuation, standard deviation values of these pulse rate and pulse fluctuation are calculated, and a determination regarding drowsiness of the driver is performed using the standard deviation values. At this time, the drowsiness level of the driver can be determined as an index of a physiological state when performing driving while feeling light drowsiness of trying to return to an alert state and resisting drowsiness.

However, since the value of the pulse rate or the pulse rate standard deviation value varies from person to person, the determination result may differ with each driver if the pulse rate standard deviation value is used for drowsiness determination as it is. Accordingly, by correcting the pulse rate standard deviation value for every driver, the influence of a variation in the value of the pulse rate of each driver on drowsiness determination is eliminated. The same is true for the pulse fluctuation low-frequency component value, the pulse fluctuation high-frequency component value, and the pulse fluctuation ratio value.

At this time, causes of a variation in the pulse feature value, such as a pulse rate, include a cause based on the driver's body state which affects drowsiness and a cause based on a traveling environment change of a vehicle. The change in the pulse feature value caused by drowsiness continues in the body for about several minutes to several hours, but the change in the pulse feature value caused by the traveling environment change of a vehicle is momentary, lasting about several seconds to tens of seconds. Specifically, when a vehicle travels in an urban area, a curved road, a road along which the driver has not driven previously, or an intersection or when a moving object is present in the vicinity of the vehicle, the pulse rate and the like of the driver rise rapidly. For this reason, the change in the pulse feature value caused by the traveling environment change of the vehicle is a cause of noise when correcting the standard deviation value of the pulse feature value (erroneous detection of drowsiness). Therefore, it is necessary to correct the standard deviation value of the pulse feature value only when the cause of a variation in the pulse feature value is based on the driver's body state.

In the present embodiment, the information regarding the traveling environment of the vehicle is acquired on the basis of the information of the navigation device 103 and the output data of the surrounding environment recognition sensor 104 and the occupant detecting sensor 105. When it is determined that the vehicle travels in any of an urban area, a curved road, a road along which the driver has not driven previously, and an intersection, when it is determined that a moving object is present in the vicinity of the vehicle, and when it is determined that a passenger is in the vehicle and the driver is moving, the standard deviation value of the pulse feature value is not corrected. In this case, light drowsiness of a driver can be detected independently for a particular driver with high precision. Therefore, drowsy driving can be effectively prevented by demanding the driver recover normal consciousness or take a rest when there is light drowsiness.

In addition, the present embodiment is not limited to the above-described. For example, in the present embodiment, a determination regarding drowsiness of a driver is performed using four pulse feature values called the value of the pulse rate, the pulse fluctuation low-frequency component value, the pulse fluctuation high-frequency component value, and the pulse fluctuation ratio value. However, it is also possible to use at least one of these four pulse feature values.

[Third Embodiment]

Figure 32:
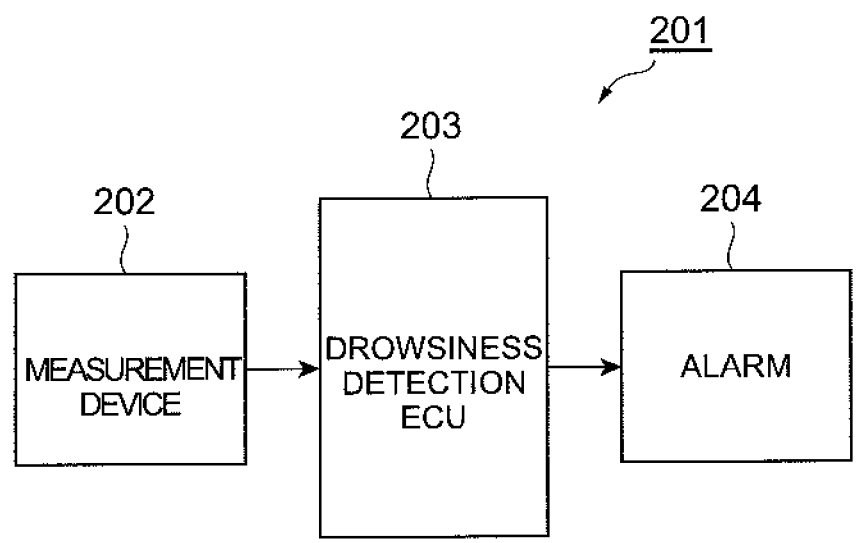
FIG. 32 is a block diagram showing the schematic configuration of a third embodiment of the drowsiness detector related to the present invention.

FIG. 32 is a block diagram showing the schematic configuration of a third embodiment of the drowsiness detector related to the present invention. In this drawing, a drowsiness detector 201 of the present embodiment is a device which is mounted in a vehicle and detects drowsiness of a driver of the vehicle. The drowsiness detector 201 includes a measurement device 202, a drowsiness detection ECU (Electronic Control Unit) 203, and an alarm 204.

The measurement device 202 is a device which measures a physiological index of the driver. Specifically, for example, an electrocardiogram system which measures a heartbeat and a plethysmograph which measures a pulse from the fingertip or forearm may be mentioned as the measurement device 202.

The drowsiness detection ECU 203 is configured to include a CPU, memories such as a ROM or a RAM, and an input and output circuit. The drowsiness detection ECU 203 is input with the measurement data of the measurement device 202, performs predetermined processing, and determines whether or not a driver is in a lightly drowsy state.

The alarm 204 is a device which notifies a driver of the occurrence of drowsiness by giving an alarm with a sound (buzzing sound), an image (screen display), vibration (vibrator), or the like.

Figure 33:
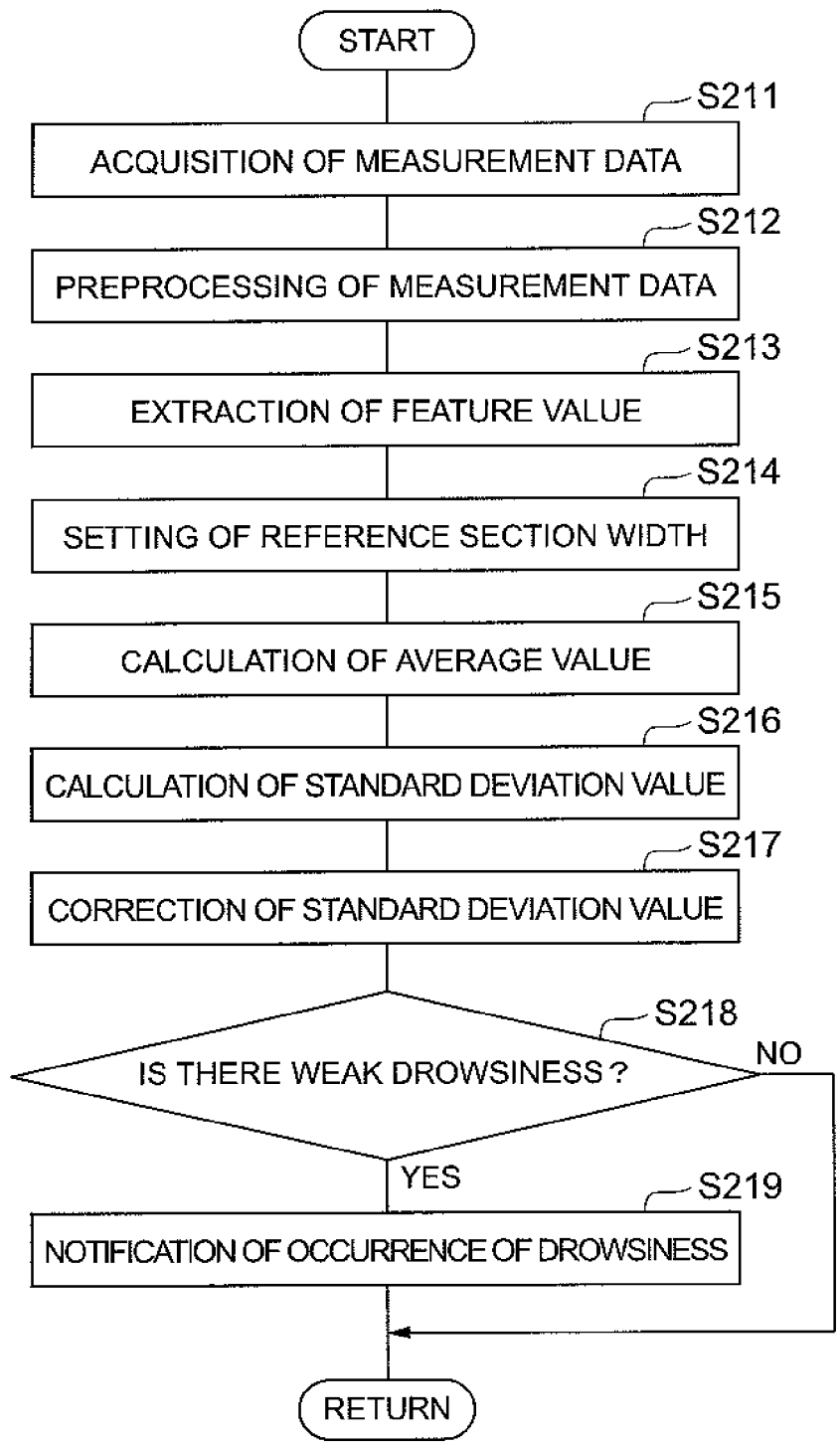
FIG. 33 is a flow chart showing the details of the procedure of drowsiness detection processing executed by a drowsiness detection ECU shown in FIG. 32.

FIG. 33 is a flow chart showing the details of the procedure of drowsiness detection processing executed by the drowsiness detection ECU 203. Here, the case of measuring a pulse of a driver with an electrocardiogram system as the measurement device 202 will be described as an example.

In this drawing, the measurement data (raw pulse data) of the measurement device 202 is acquired first (step S211), and the measurement data is preprocessed (step S212). Specifically, first, components in a predetermined pass band (for example, 0.1 Hz to 30 Hz) are extracted by performing band pass filter (BPF) processing on the raw pulse data in order to remove noise of the pulse data.

Figure 34:
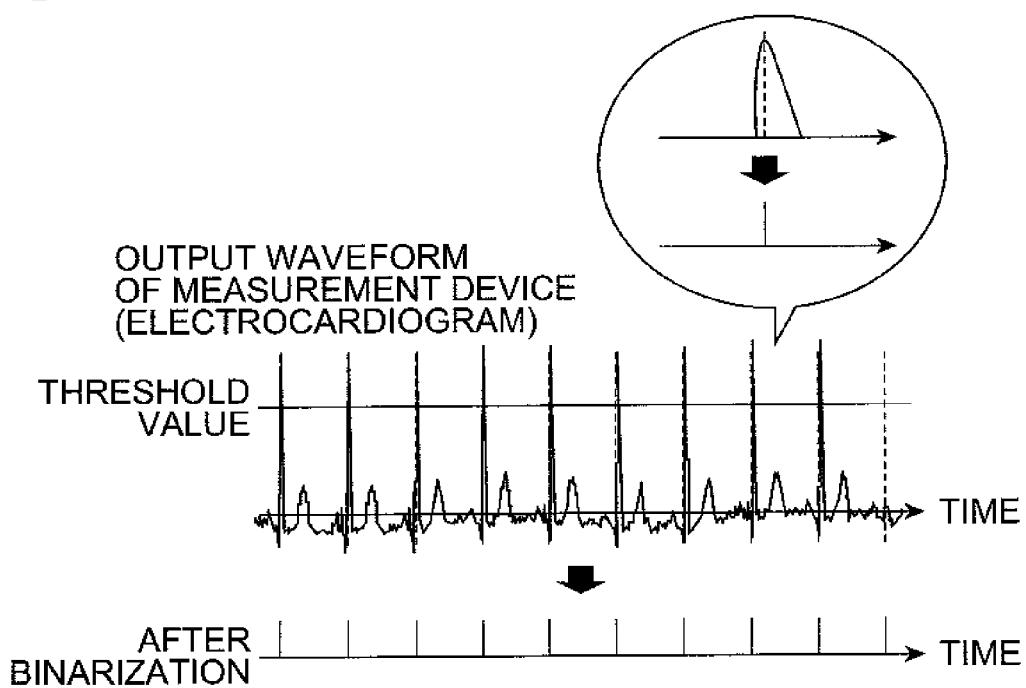
FIG. 34 is a waveform chart showing an example of an output waveform of a measurement device shown in FIG. 32 and a binarized waveform.

Then, as shown in FIG. 34, the waveform of the pulse data obtained by performing BPF processing is binarized by comparing it with the threshold value set in advance. At this time, the binarization is performed so that it becomes "1" at a timing when each R-wave portion of the waveform of the pulse data is a maximum (refer to the enlarged view in FIG. 34).

Figure 35:
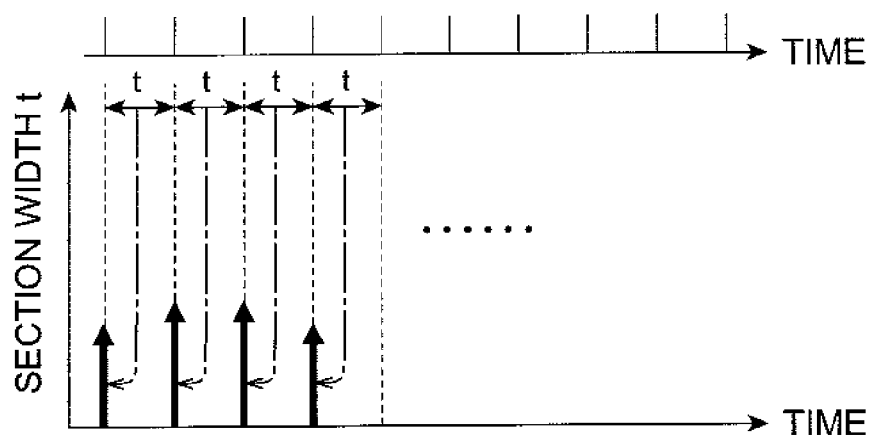
FIG. 35 is a waveform chart showing an example of the section width and a periodic time series of a binarized waveform.
Figure 35:
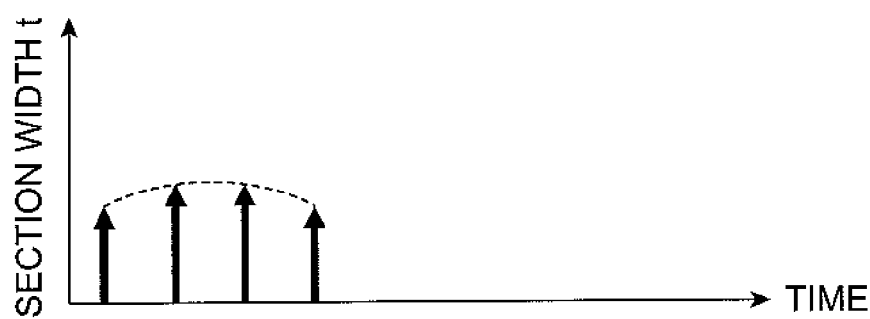

Then, as shown in FIG. 35A, a section width (time interval) t is calculated at each timing when the binary data becomes "1", and a graph having each section width t as a vertical axis is generated. At this time, the section width t is equivalent to a pulse period of a driver.

Figure 36:
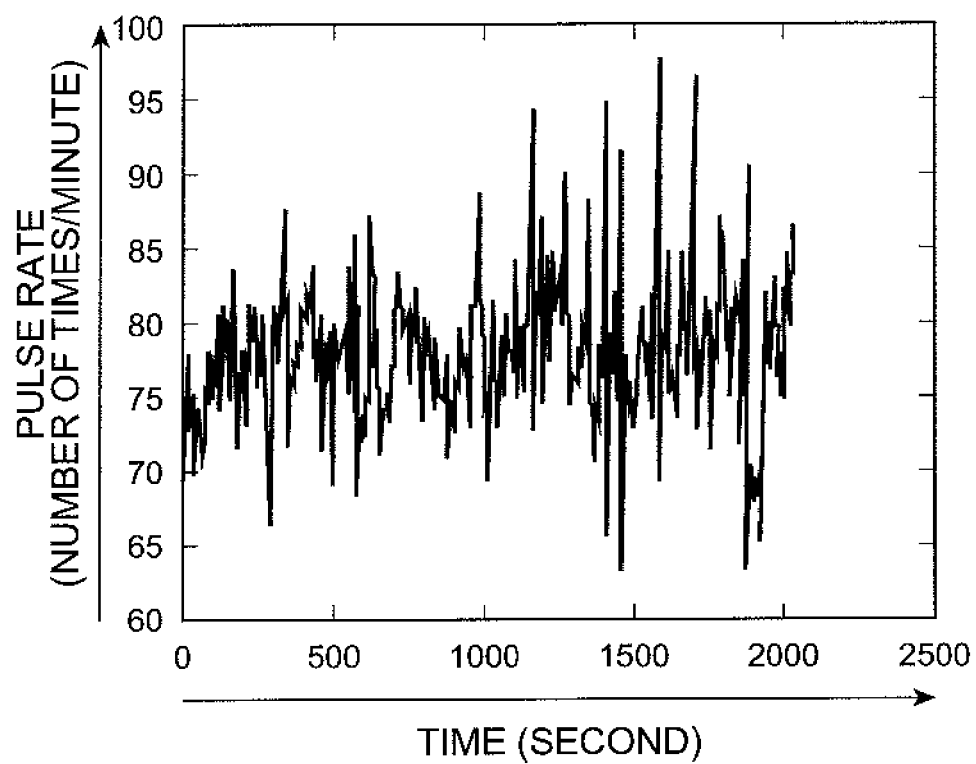
FIG. 36 is a waveform chart showing an example of a periodic time series of a pulse rate.

Then, as shown in FIG. 35B, a curve (refer to the broken line) of the pulse period is obtained by interpolating the graph of the pulse period, and the time-series data of the pulse period is acquired. Then, as shown in FIG. 36, the vertical axis unit of the time-series data of the pulse period is converted into the pulse rate per minute, for example. Accordingly, the value of the pulse rate of the driver can be acquired as one of the pulse feature values.

Figure 37:
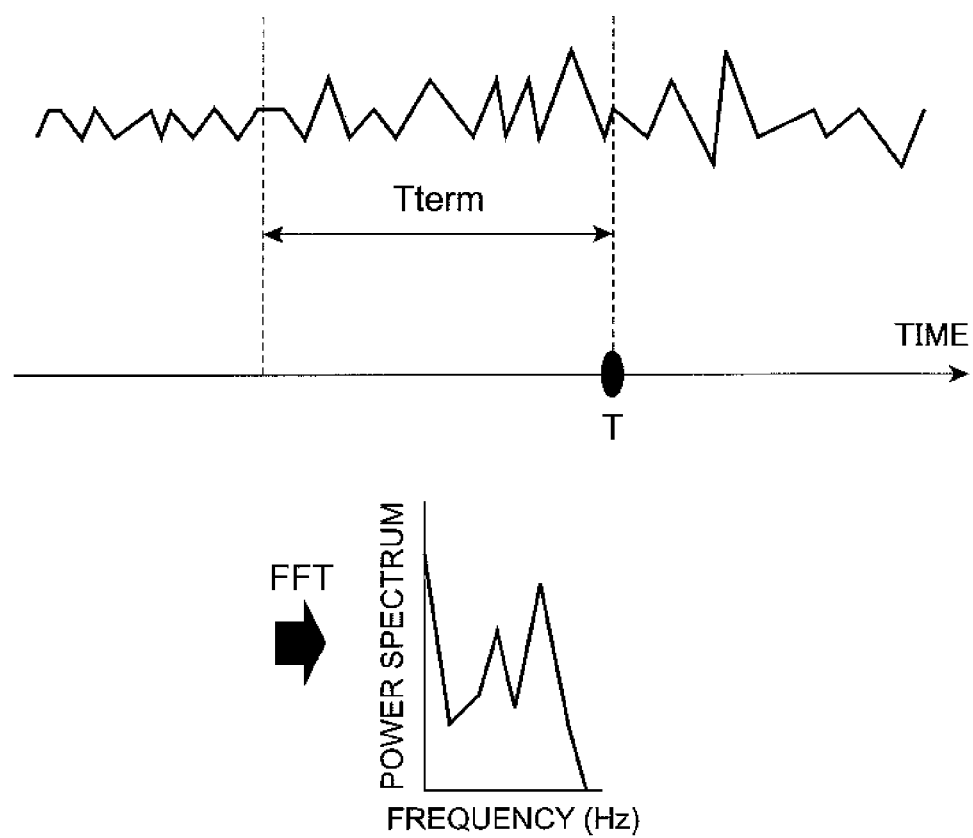
FIG. 37 is a waveform chart showing an example of a waveform obtained by performing FFT processing on a periodic time series of a pulse rate.

Subsequently, a pulse fluctuation is extracted as another pulse feature value of the driver (step S213). Specifically, regarding the time-series data (refer to FIG. 36) of the pulse period, as shown in FIG. 37, fast Fourier transform (FFT) is performed on the analysis unit section width $T_{term}$ before the reference time T (arbitrary time stamp) so that a power (amplitude) spectrum over a frequency component is acquired.

Figure 38:
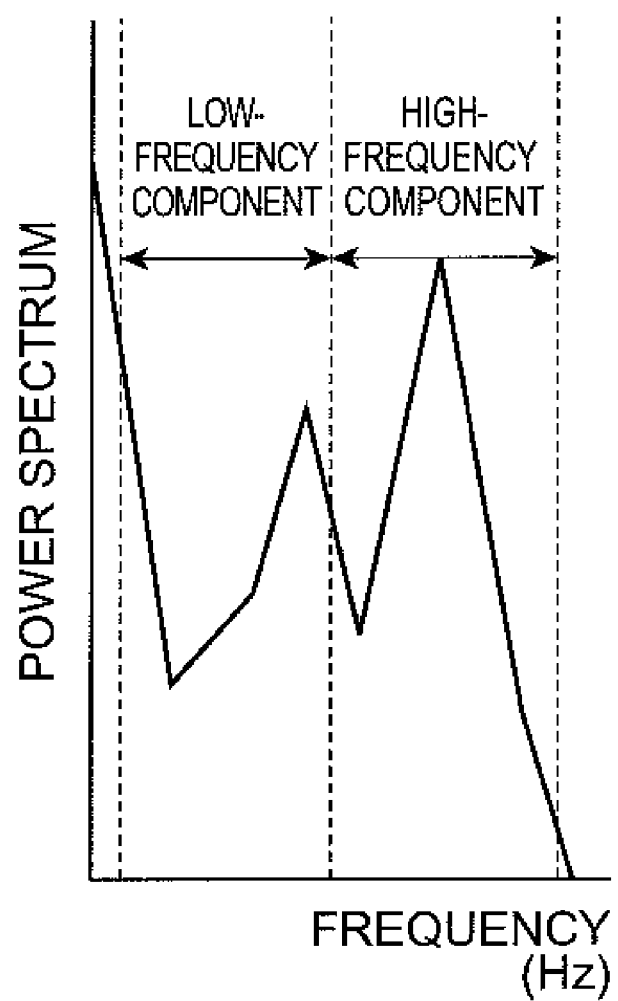
FIG. 38 is a waveform chart showing a state where two frequency bands are set for a waveform obtained by performing FFT processing.

Then, as shown in FIG. 38, two frequency bands (a low-frequency component and a high frequency component) are set for the power spectrum obtained for every analysis unit section width $T_{term}$ by fast Fourier transform. These frequency bands are bands where a pulse fluctuation (change) appears easily. In addition, the amplitude spectrum is integrated for each frequency band.

Figure 39:
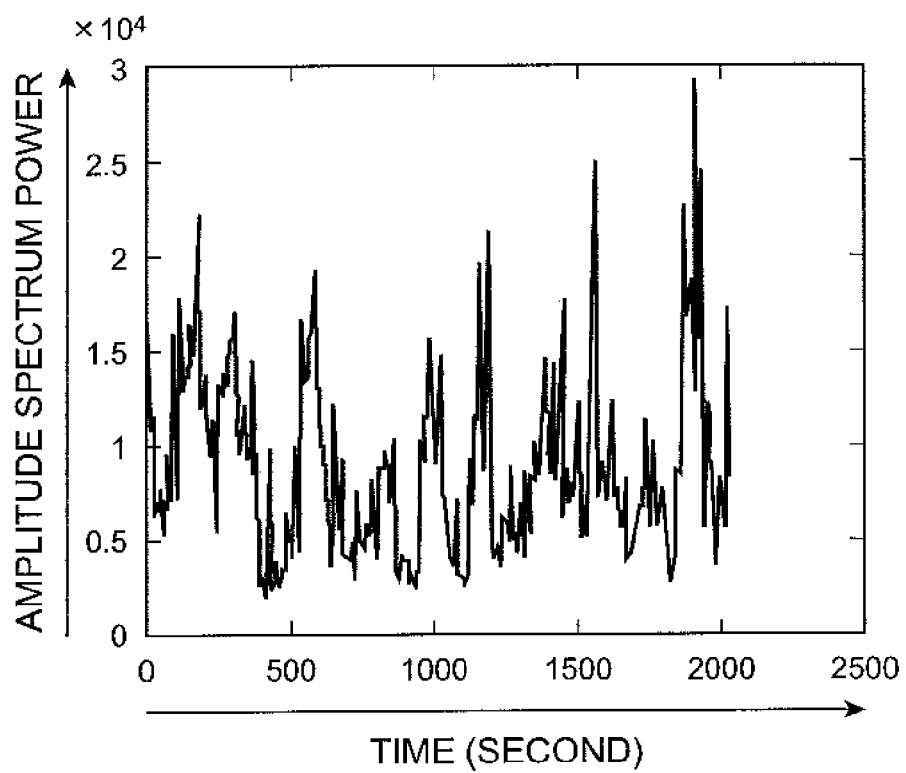
FIG. 39 is a waveform chart showing an example of a periodic time series of a pulse fluctuation.

By repeatedly performing the fast Fourier transform processing, the setting processing of a frequency band, and the integration processing, the time-series data of the amplitude spectrum power for each frequency band is acquired, as shown in FIG. 39. The time-series data of the amplitude spectrum power is time-series data of the pulse fluctuation. As a result, a pulse fluctuation low-frequency component value indicating the movement of the sympathetic nerve and a pulse fluctuation high-frequency component value indicating the movement of the parasympathetic nerve are acquired. In addition, the ratio (pulse fluctuation ratio value) of the pulse fluctuation low-frequency component value and the pulse fluctuation high-frequency component value is acquired by dividing the pulse fluctuation low-frequency component value by the pulse fluctuation high-frequency component value.

Then, the reference section width (reference time width) of the pulse feature value referred to in order to acquire the standard deviation of the pulse feature value is set (step S214). Setting of the reference time width of the pulse feature value is performed for each of the value of the pulse rate, the pulse fluctuation low-frequency component value, the pulse fluctuation high-frequency component value, and the pulse fluctuation ratio value.

Figure 40:
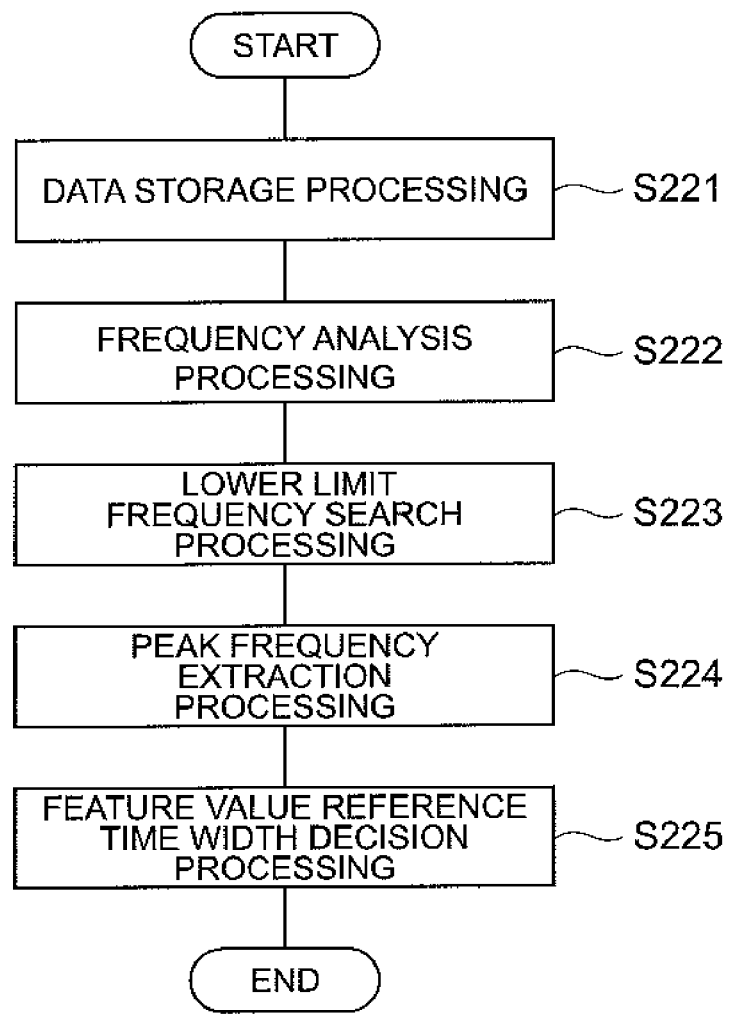
FIG. 40 is a flow chart showing the details of the procedure of processing for setting the reference time width of the pulse feature value shown in FIG. 33.

FIG. 40 is a flow chart showing the details of the procedure of processing for setting the reference time width of the pulse feature value. Here, a value of the pulse rate will be described below as an example of the pulse feature value.

Figure 41:
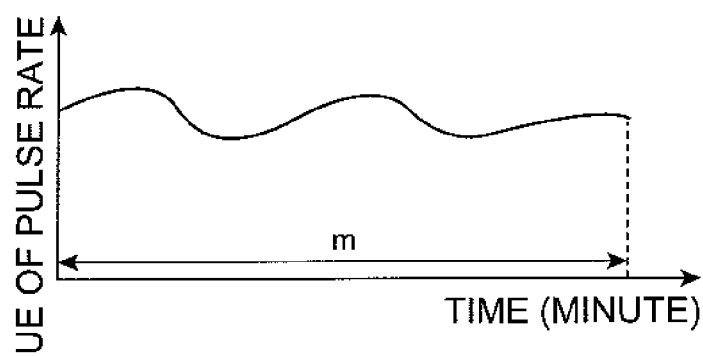
FIG. 41 is a waveform chart showing a method of performing data storage processing and frequency analysis processing shown in FIG. 40.
Figure 41:
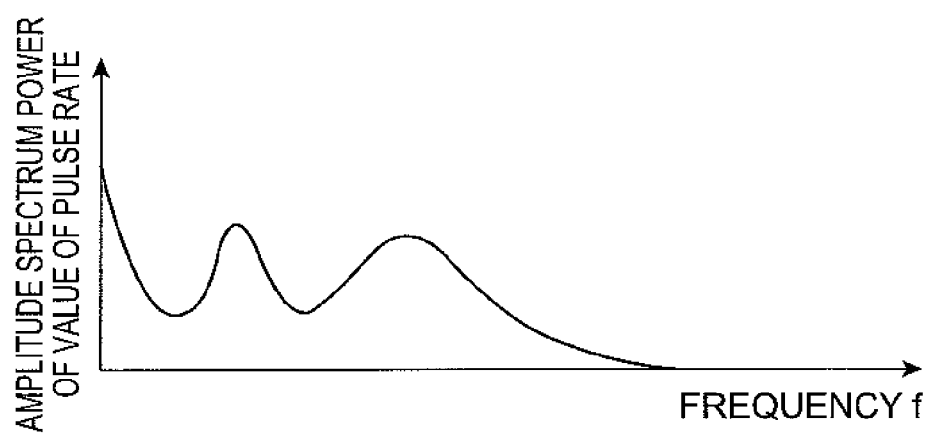

In this drawing, first, the time-series data of the pulse feature value is stored in a data storage buffer for reference time width determination (step S221). At this time, for example, the value of the pulse rate (refer to FIG. 39) is divided for every arbitrary length (about several minutes) m as shown in FIG. 41A, and it is stored in the data storage buffer for reference time width determination.

Then, the frequency analysis of the pulse feature value stored in the data storage buffer for reference time width determination is performed (step S222). Specifically, as shown in FIG. 41B, the frequency spectrum distribution of the value of the pulse rate is acquired by performing a fast Fourier transform (FFT) operation on the value of the pulse rate stored in the data storage buffer.

Figure 42:
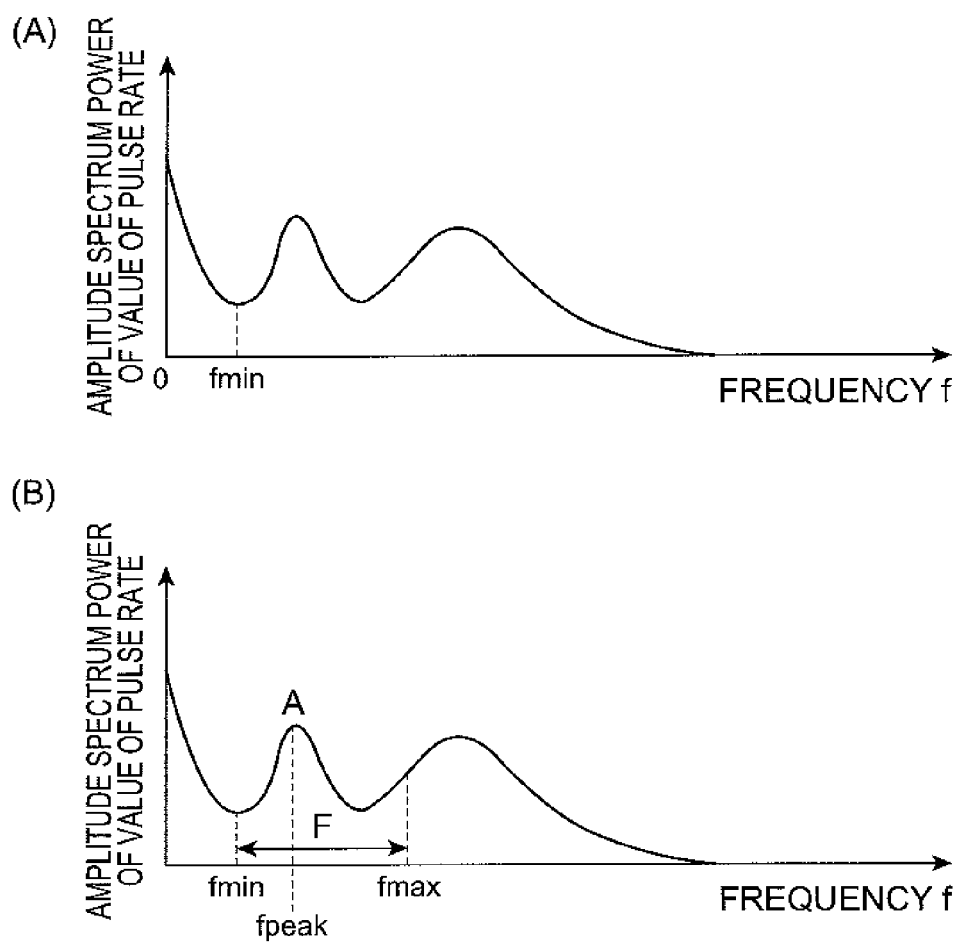
FIG. 42 is a waveform chart showing a method of performing lower limit frequency search processing and peak frequency extraction processing shown in FIG. 40.

Then, as shown in FIG. 42A, the first minimum value (point which protrudes to the lower side of frequency spectrum distribution) when viewed from a frequency f=0 in the frequency spectrum distribution of the value of the pulse rates is searched as a lower limit frequency $f_{min}$ (step S223).

Then, as shown in FIG. 42B, a peak frequency $f_{peak}$ corresponding to the value A, at which initial rising of the amplitude spectrum power of the value of the pulse rate becomes a maximum in a frequency range F having the lower limit frequency $f_{min}$ as a starting point, is extracted (step S224). Here, the frequency range F is obtained by setting a wide range of the value of the pulse rate that most people can have from a medical point of view. The frequency $f_{peak}$ is a frequency at which individual features appear most and more specifically, is a frequency at which especially a change of drowsiness in the value of the pulse rate tends to occur.

Then, the reference section width of the pulse feature value is calculated from the following calculation expression using such a frequency $f_{peak}$.

Reference section width of the pulse feature value=1/$f_{peak}$

By extracting the peak frequency $f_{peak}$ in the frequency range F as a place where drowsiness noticeably occurs as described above, an effect of data noise is removed to determine a drowsy state (described later).

After returning to FIG. 33 to set the reference time width of the pulse feature value by executing step S214 described above, the value of the pulse rate, the pulse fluctuation low-frequency component value, the pulse fluctuation high-frequency component value, and the pulse fluctuation ratio value are cut by the reference section width (the total number of data items: N), and the average value in this section is calculated (step S215).

Cut value of the pulse rate=$\{X_1, X_2, X_3, \ldots, X_N\}$

Cut pulse fluctuation low-frequency component value=$\{Y_1, Y_2, Y_3, \ldots, Y_N\}$ Cut pulse fluctuation high-frequency component value=$\{Z_1, Z_2, Z_3, \ldots, Z_N\}$ Cut pulse fluctuation ratio value=$\{W_1, W_2, W_3, \ldots, W_N\}$ Then, in the same manner as described above, each of the value of the pulse rate, the pulse fluctuation low-frequency component value, the pulse fluctuation high-frequency component value, and the pulse fluctuation ratio value is cut by the reference section width, and the standard deviation values of the value of the pulse rate, the pulse fluctuation low-frequency component value, the pulse fluctuation high-frequency component value, and the pulse fluctuation ratio value in this section are calculated by the calculation expressions shown in the above expressions 2 to 5 (step S216).

Subsequently, the standard deviation values of the value of the pulse rate, the pulse fluctuation low-frequency component value, the pulse fluctuation high-frequency component value, and the pulse fluctuation ratio value are corrected (step S217). The correction of these standard deviation values is performed as follows.

That is, first, the pulse rate standard deviation value, the pulse fluctuation low-frequency component standard deviation value, the pulse fluctuation high-frequency component standard deviation value, and the pulse fluctuation ratio standard deviation value, which were acquired in step S216, and a value of the pulse rate, a pulse fluctuation low-frequency component value, a pulse fluctuation high-frequency component value, and a pulse fluctuation ratio value, which are used for correction, are stored in a buffer which stores standard deviation values to be corrected.

Then, the pulse rate standard deviation value, the pulse fluctuation low-frequency component standard deviation value, the pulse fluctuation high-frequency component standard deviation value, and the pulse fluctuation ratio standard deviation value are corrected using the calculation expression shown in the above expression 6, thereby acquiring a corrected pulse rate standard deviation value, a corrected pulse fluctuation low-frequency component standard deviation value, a corrected pulse fluctuation high-frequency component standard deviation value, and a corrected pulse fluctuation ratio standard deviation value.

Since the value of the pulse rate or the pulse rate standard deviation value varies from person to person, the determination result may differ depending on a subject if the pulse rate standard deviation value is used for drowsiness determination (described later) as it is. Accordingly, by correcting the pulse rate standard deviation value for every subject, the influence of a variation in the value of the pulse rate of each subject on drowsiness determination is eliminated. The same is true for the pulse fluctuation low-frequency component value, the pulse fluctuation high-frequency component value, and the pulse fluctuation ratio value.

Then, it is determined whether or not the driver is lightly drowsy using the corrected pulse rate standard deviation value, the corrected pulse fluctuation low-frequency component standard deviation value, the corrected pulse fluctuation high-frequency component standard deviation value, and the corrected pulse fluctuation ratio standard deviation value (step S218).

Figure 43:
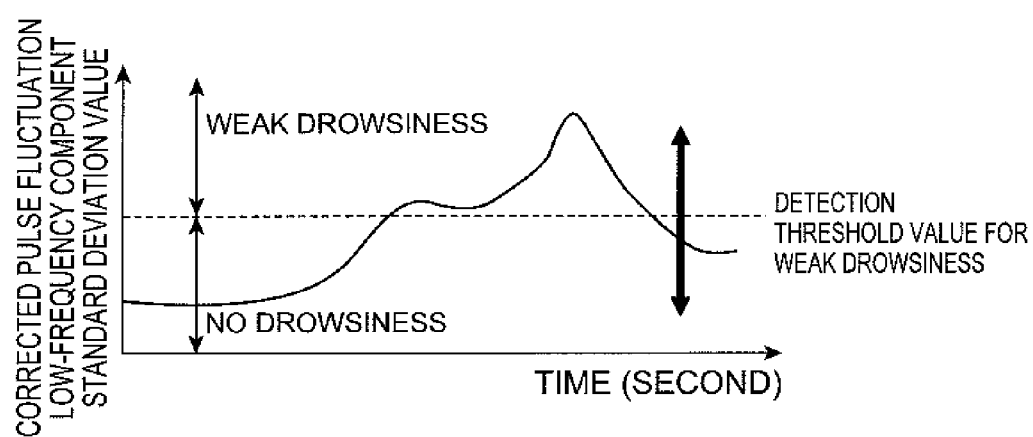
FIG. 43 is a waveform chart showing an example of a method of determining drowsiness with a corrected pulse fluctuation low-frequency component standard deviation value.

An example of a method of determining drowsiness with the corrected pulse fluctuation low-frequency component standard deviation value is shown in FIG. 43. In the method shown in this drawing, the corrected pulse fluctuation low-frequency component standard deviation value is compared with a detection threshold value for light drowsiness set in advance. When the corrected pulse fluctuation low-frequency component standard deviation value is higher than the detection threshold value for light drowsiness, it is determined to be a state where there is light drowsiness. When the corrected pulse fluctuation low-frequency component standard deviation value is lower than the detection threshold value for light drowsiness, it is determined to be a state where there is no drowsiness.

Moreover, also in the cases where the corrected pulse rate standard deviation value, the corrected pulse fluctuation high-frequency component standard deviation value, and the corrected pulse fluctuation ratio standard deviation value are used, it can be similarly determined whether or not there is light drowsiness.

When it is determined that there is no drowsiness by the above-described method in step S218, the process returns to step S211 to repeatedly execute the processing in steps S211 to S218. On the other hand, when it is determined that there is light drowsiness in step S218, the occurrence of drowsiness is notified to the driver by controlling the alarm 204 (step S219), and then the process returns to step S211.

In the above, steps S211 to S213 shown in FIG. 33 form a pulse feature value extracting means for extracting the pulse feature value from the heartbeat or a pulse of a subject. Step S214 forms a reference time width setting means for setting the pulse feature value reference time width for referring to the pulse feature value. Steps S215 and S216 form a statistical distribution calculating means for calculating the statistical distribution of the pulse feature values in the feature value reference time width. Steps S217 and S218 form a drowsiness level determining means for determining the drowsiness level of a subject using the statistical distribution of the pulse feature values.

As described above, in the present embodiment, attention is paid to a pulse influenced by autonomic nerve activity relevant to the occurrence of drowsiness, a heartbeat or a pulse of the driver is measured to extract the pulse rate and a pulse fluctuation, standard deviations of these pulse rate and pulse fluctuation are calculated, and a determination regarding drowsiness of the driver is performed using the standard deviations. At this time, the drowsiness level of the driver can be determined as an index of a physiological state when performing driving while feeling light drowsiness of trying to return to an alert state and resisting drowsiness.

Here, when calculating the pulse rate and the standard deviation of a pulse fluctuation, the reference time width of the pulse feature value is set as follows. That is, the frequency spectrum distribution is generated by performing FFT processing on the pulse feature value, the lower limit frequency $f_{min}$ which is the first minimum value in the frequency spectrum distribution is searched, and the peak frequency $f_{peak}$ corresponding to the maximum value A of the amplitude spectrum power in the predetermined frequency range F having the lower limit frequency $f_{min}$ as a starting point is extracted. The frequency $f_{peak}$ is a frequency at which features of a driver appear most as described above. Accordingly, by taking the inverse of such a peak frequency $f_{peak}$ and setting it as a reference time width, a reference time width suitable for a driver can be obtained. This makes it possible to obtain a standard deviation suitable for a driver.

In this case, light drowsiness of a driver can be detected with high precision regardless of the driver. Therefore, drowsy driving can be effectively prevented by demanding the driver recover normal consciousness or take a rest when there is light drowsiness.

In addition, the present embodiment is not limited to the above-described. For example, in the present embodiment, a determination regarding drowsiness of a driver is performed using four pulse feature values called the value of the pulse rate, the pulse fluctuation low-frequency component value, the pulse fluctuation high-frequency component value, and the pulse fluctuation ratio value. However, it is also possible to use at least one of these four pulse feature values.

In addition, in the present embodiment, determination regarding light drowsiness of a driver is performed by calculating the standard deviation of the pulse feature value. However, the present invention may also be applied when determining drowsiness of a driver using those (for example, only an average value) other than the standard deviation as the statistical distribution of the pulse feature value.

In addition, although the drowsiness detector 201 of the present embodiment is mounted in a vehicle, it may also be applied to those which detect the drowsiness level of a subject other than a driver of a vehicle.

Industrial Applicability

According to the present invention, it becomes possible to detect light drowsiness of a subject with high precision.

Reference Signs List 1, 101, 201: drowsiness detector
2: measurement device (measurement means)
3: drowsiness detection ECU (pulse feature value extracting means, variation distribution calculating means, drowsiness level determining means, average value calculating means, reference time width setting means)
102: physiological index measuring device (measurement means)
106: drowsiness detection ECU (pulse feature value extracting means, standard deviation calculating means, drowsiness level determining means)
202: measurement device (measurement means)
203: drowsiness detection ECU (pulse feature value extracting means, reference time width setting means, drowsiness level determining means)

The invention claimed is:

1. A drowsiness detector comprising:
a measurement means for measuring a heartbeat or a pulse of a subject;
a pulse feature value extracting means for extracting a pulse feature value from the heartbeat or the pulse measured by the measurement means;
a variation distribution calculating means for calculating variation distribution of the pulse feature value extracted by the pulse feature value extracting means; and
a drowsiness level determining means for determining a drowsiness level of the subject using the variation distribution of the pulse feature value calculated by the variation distribution calculating means,
wherein the variation distribution calculating means has a means for calculating a standard deviation of the pulse feature value as the variation distribution of the pulse feature value and a means for correcting the standard deviation of the pulse feature value by dividing the standard deviation of the pulse feature value by the pulse feature value acquired in a state where there is no drowsiness, and the drowsiness level determining means determines the drowsiness level of the subject on the basis of the standard deviation of the pulse feature value, and the pulse feature value includes at least one of a pulse fluctuation low-frequency component relevant to the activity of the sympathetic nerve, a pulse fluctuation high-frequency component relevant to the activity of the parasympathetic nerve, and a ratio of the pulse fluctuation low-frequency component and the pulse fluctuation high-frequency component.

2. The drowsiness detector according to claim 1, further comprising:

an average value calculating means for calculating an average value of the pulse feature value extracted by the pulse feature value extracting means, wherein the variation distribution calculating means calculates a standard deviation of the pulse feature value as the variation distribution of the pulse feature value, and the drowsiness level determining means determines the drowsiness level of the subject on the basis of the standard deviation of the pulse feature value and the average value of the pulse feature value.

3. The drowsiness detector according to claim 2, further comprising:

a reference time width setting means for setting a reference time width of the pulse feature value referred to in order to obtain the standard deviation of the pulse feature value, wherein the variation distribution calculating means calculates the standard deviation of the pulse feature value within the reference time width of the pulse feature value.

4. The drowsiness detector according to claim 3, wherein the reference time width setting means extracts a peak frequency by frequency analysis of the pulse feature value and sets a period corresponding to the peak frequency as the reference time width.

5. The drowsiness detector according to claim 1 which detects drowsiness of a driver of a vehicle, wherein a standard deviation calculating means for calculating a standard deviation of the pulse feature value extracted by the pulse feature value extracting means is provided, and the drowsiness level determining means corrects the standard deviation of the pulse feature value with the pulse feature value according to a traveling environment of the vehicle and determines the drowsiness level of the driver using the distribution of a standard deviation of the pulse feature value after correction.

6. The drowsiness detector according to claim 5, wherein the drowsiness level determining means does not correct the standard deviation of the pulse feature value when it is detected that the vehicle travels in any of an urban area, a curved road, a road along which the driver has not driven previously, and an intersection.

7. The drowsiness detector according to claim 5, wherein the drowsiness level determining means does not correct the standard deviation of the pulse feature value when it is detected that a moving object is present in the vicinity of the vehicle.

8. The drowsiness detector according to claim 5, wherein the drowsiness level determining means does not correct the standard deviation of the pulse feature value when it is detected that a passenger is in the vehicle and the driver is moving.

9. The drowsiness detector according to claim 5 which corrects the standard deviation of the pulse feature value with the pulse feature value obtained by excluding the pulse feature value acquired in a traveling environment where conscious attention tends to be stimulated.

10. The drowsiness detector according to claim 1, wherein a reference time width setting means for setting a feature value reference time width for referring to the pulse feature value is provided, the drowsiness level determining means calculates statistical distribution of the pulse feature value within the feature value reference time width and determines the drowsiness level of the subject, and the reference time width setting means generates frequency spectrum distribution of the pulse feature value by frequency analysis of the pulse feature value and calculates the feature value reference time width by extracting a frequency of a rising peak of the frequency spectrum.

11. The drowsiness detector according to claim 10, wherein the reference time width setting means extracts a peak frequency at which a spectrum becomes a maximum within a frequency range having an initial minimum value as a starting point in the frequency spectrum distribution.

12. The drowsiness detector according to claim 10, wherein the reference time width setting means sets the inverse of the peak frequency as the feature value reference time width.

13. The drowsiness detector according to claim 10, wherein the drowsiness level determining means calculates a standard deviation of the pulse feature value as the statistical distribution of the pulse feature value.

14. The drowsiness detector according to claim 10 which extracts a peak indicating a feature of an individual from the frequency spectrum distribution of the pulse feature value and refers to the pulse feature value from a time width based on the peak frequency.

* * * * *